United States Patent [19]

Bock et al.

[11] Patent Number: 4,663,321
[45] Date of Patent: May 5, 1987

[54] TRIAZOLOBENZODIAZEPINES AND PHARMACEUTICAL USE

[75] Inventors: Mark G. Bock, Hatfield; Ben E. Evans, Lansdale; Roger M. Freidinger, Hatfield, all of Pa.

[73] Assignee: Merck & Co., Inc., Rahway, N.J.

[21] Appl. No.: 741,971

[22] Filed: Jun. 10, 1985

Related U.S. Application Data

[63] Continuation-in-part of Ser. No. 624,850, Jun. 26, 1984, abandoned.

[51] Int. Cl.$^4$ .................. A61K 31/55; C07D 487/04
[52] U.S. Cl. ..................... 514/220; 540/563; 540/564; 540/565; 540/566; 540/542
[58] Field of Search ............ 260/245.5, 244.4, 243.3; 514/220; 540/563, 564, 565, 566, 542

[56] References Cited

U.S. PATENT DOCUMENTS 3,880,877  4/1975  Sellstedt et al. ................. 260/245.5
4,046,772  9/1977  Kuwada et al. ................. 260/245.5
4,180,668 12/1979  Hester ........................... 260/245.5 X

*Primary Examiner*—Richard L. Raymond
*Attorney, Agent, or Firm*—Richard A. Elder; Hesna J. Pfeiffer; Samuel B. Abrams

[57] ABSTRACT

Triazolobenzodiazepines of the formula:

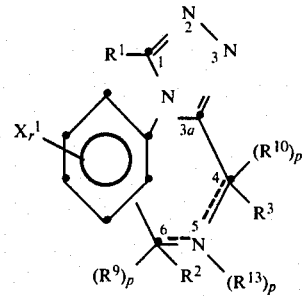

are disclosed which are antagonists of cholecystokinin (CCK).

12 Claims, No Drawings

TRIAZOLOBENZODIAZEPINES AND PHARMACEUTICAL USE

CROSS-REFERENCE

This application is a continuation-in-part of U.S. patent application Ser. No. 624,850, filed June 26, 1984, now abandoned.

The benzodiazepinones (Formula II) which are the starting materials for the compounds of Formula I are described in U.S. patent application, Ser. No. 741,972, filed June 10, 1985, which is a continuation-in-part of U.S. patent application, Ser. No. 705,272, filed Feb. 25, 1985, now abandoned, which in turn is a continuation-in-part of U.S. patent application, Ser. No. 624,854, field June 26, 1984, now abandoned which is incorporated herein by reference.

U.S. Ser. No. 624,853, filed June 26, 1984, entitled "Acylaminophenyl-ketones and Amines", is incorporated herein by reference.

BACKGROUND OF THE INVENTION

Cholecystokinin (CCK) is a neuropeptide composed of thirty-three aminoacids in its originally isolated form. See: Mutt and Jorpes, *Biochem. J.* 125 678 (1971). Also occurring in circulation are 39, 12 and 8 amino acid forms. The carboxyl terminal octapeptide (CCK-8) is the minimum active sequence. Gastrin occurs in 34, 17, and 14 amino acid forms in circulation and is related to CCK by identity of the C-terminal pentapeptides Gly-Trp-Met-Asp-Phe-NH$_2$. Gastrin and CCK exist in both gastrointestinal tissue and the central nervous system. V. Mutt, *Gastrointenstinal Hormones*, G. B. J. Glass, Ed., Raven Press, N.Y., p. 169 and G. Nisson, ibid, p. 127. CCK is believed to play an important role in appetite regulation and CCK may be a physiological satiety hormone. G. P. Smith, *Eating and Its Disorders*, A. J. Stunkard and E. Stellar, Eds, Raven Press, New York, 1984, p. 67.

Among additional effects of CCK are stimulation of colonic motility, stimulation of gall bladder contraction, stimulation of pancreatic enzyme secretion, and inhibition of gastric emptying. CCK reportedly co-exists with dopamine in certain mid-brain neurons and thus may also play a role in the functioning of dopaminergic systems in the brain, as well as serving as a neurotransmitter in its own right. See: A. J. Prange et al., "Peptides in the Central Nervous System", *Ann. Repts. Med. Chem.* 17 31, 33 (1982) and reference cited therein; J. A. Williams, *Biomed. Res.* 3, 107 (1982); and J. E. Morley, *Life Sci.* 30, 479, (1982).

The primary role of gastrin appears to be stimulation of secretion of water and electrolytes from the stomach and it is therefore involved in control of gastric acid secretion.

CCK antagonists are useful in the treatment and prevention of CCK-related disorders of the gastrointestinal, central nervous and appetite regulatory systems of animals, especially humans. Three distinct chemical classes of CCK receptor antagonists have been reported. One class comprises derivatives of cyclic nucleotides; detailed structure-function studies have demonstrated that of the various members of this class, dibutyryl cyclic GMP is the most potent. See; N. Barlos et al., *Am. J. Physiol.*, 242, G 161 (1982) and P. Robberecht et al., *Mol., Pharmacol.*, 17, 268 (1980). The second class comprises peptide antagonists which are C-terminal fragments and analogs of CCK. Recent structure-function studies have shown that both shorter C-terminal fragments of CCK (Boc-Met-Asp-Phe-NH$_2$, Met-Asp-Phe-NH$_2$) as well as longer CCK fragments Cbz-Tyr(-SO$_3$H)-Met-Gly-Trp-Met-Asp-NH$_2$) can function as CCK antagonists. See: R. T. Jensen et al., *Biochem. Biophys. Acta.*, 757, 250 (1983) and M. Spanarkel et al., *J. Biol. Chem.*, 258, 6746 (1983). The third class of CCK receptor antagonists comprises the amino acid derivatives; proglumide, a derivative of glutaramic acid, and the N-acyl tryptophans including para-chlorobenzoyl-L-tryptophan (benzotript). See W. F. Hahne et al., *Proc. Natl. Acad. Sci. U.S.A.*, 78, 6304 (1981) and R. T. Jensen et al., *Biochem. Biophys. Acta.*, 761, 269 (1983). All of these compounds are relatively weak antagonists of CCK (IC$_{50}$: $10^{-4}$–$10^{-6}$M; generally, $10^{-4}$M but down to $10^{-6}$M in the case of peptides). The peptide antagonists have substantial stability and absorption problems.

Gastrin antogonists are useful in the treatment and prevention of gastrin-related disorders of the gastrointestinal systems of humans and animals such as ulcers, Zollinger-Ellison syndrome, antral G cell hyperplasia and other conditions in which reduced gastrin activity is of therapeutic value. There are no effective receptor antagonists of the in vivo effects of gastrin. J. S. Morley, *Gut Pept. Ulcer Proc.*, Hiroshima Symp. 2nd, 1983, page 1. Very weak in vitro antagonists such as proglumide and certain peptides have been reported, J. Martinez, *J. Med. Chem.*, 27, 1957 (1984).

The benzodiazepine (BZD) structure class has been widely exploited as therapeutic agents especially as central nervous system (CNS) drugs. These compounds exhibit strong binding to "benzodiazepine receptors" in vitro, but have not been reported to bind to CCK or gastrin receptors. The large majority of reported BZD's do not contain substituents attached to the 3-position of the seven-membered ring. It is well known in the art that 3-substituents result in decreasing CNS activity (non-CCK related), especially as these substituents increase in size. It has been demonstrated that the preferred stereochemistry at position 3 for this CNS activity is S, which would correspond to an L-amino acid such as L-tryptophan. The compounds of Formula I are distinguished from BZD's of the prior art especially by the presence of 3-substituents. The formula I compounds bind strongly to CCK receptors, but only weakly to BZD receptors, especially with increasing size of the substituents. The preferred stereochemistry of Formula I compounds is opposite to that of prior art BZD's.

SUMMARY OF THE INVENTION

It has now been found that compounds of Formula I are antagonists of cholecystokinin (CCK). These CCK antagonists are useful in the treatment and prevention of CCK-related disorders of the gastrointestinal, central nervous and appetite regulatory systems of mammals, especially humans. The compounds of Formula I are also gastrin antagonists. They are useful in the treatment and prevention of gastrointestinal ulcers, Zollinger-Ellison syndrome, antral G cell hyperplasia, and other conditions in which reduced gastrin activity is of therapeutic value.

DETAILED DESCRIPTION OF THE INVENTION

The compounds of this invention are those of Formula I:

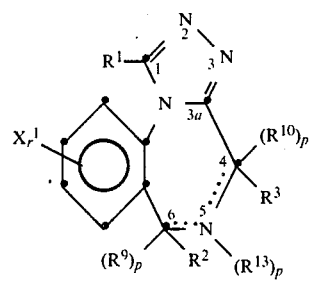

wherein
R[1] is H, OH, loweralkyl, cycloloweralkyl, loweralkynyl, loweralkenyl, substituted or unsubstituted phenyl (wherein the substituents may be 1 or 2 of halo, loeralkyl, loweralkoxy, or hydroxy), —(CH$_2$)$_m$NR[4]R[5], CX$_3$[10], or —(CH$_2$)$_n$COOR[6];

R[2] is H, loweralkyl, substituted or unsubstituted phenyl (wherein the substituents may be 1 or 2 of halo, loweralkyl, loweralkoxy, loweralkylthio, carboxyl, carboxyloweralkyl, nitro, —CF$_3$,

or hydroxy), or —(CH$_2$)$_m$COOR[6];
R[3] is

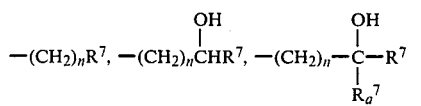

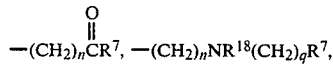

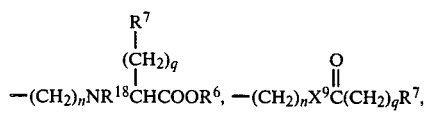

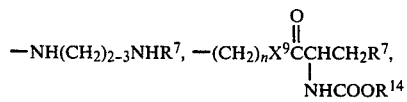

—NH(CH$_2$)$_{2-3}$NHCOR[7],

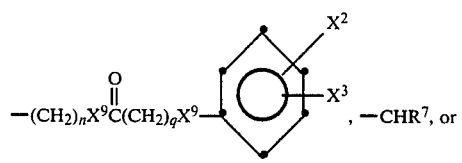

—(CH$_2$)$_n$NR[18]SO$_2$(CH$_2$)$_q$R[7],

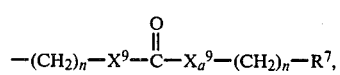

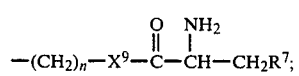

R[4] and R[5] are independently H, loweralkyl, or cycloloweralkyl or are connected to form a hetero ring

wherein n is 2–6;

R[6] is H, loweralkyl, cycloloweralkyl, substituted or unsubstituted phenyl (wherein the substituents may be 1 or 2 of halo, loweralkyl, loweralkoxy, nitro, or CF$_3$), or substituted or unsubstituted phenylloweralkyl (wherein the substituents may be 1 or 2 of halo, loweralkyl, loweralkoxy, nitro, or CF$_3$);

R[7] and R$_a$[7] are independently α- or β-naphthyl, substituted or unsubstituted phenyl (wherein the substituents may be 1 to 2 of halo, —NO$_2$, —OH, —NR[4]R[5], loweralkoyl, cyano, phenyl, trifluoromethyl, acetylamino, acetyloxy, loweralkylthio, SCF$_3$, C≡CH, CH$_2$SCF$_3$, OCHF$_2$, SH, S-phenyl, PO$_3$H, or loweralkoxy),

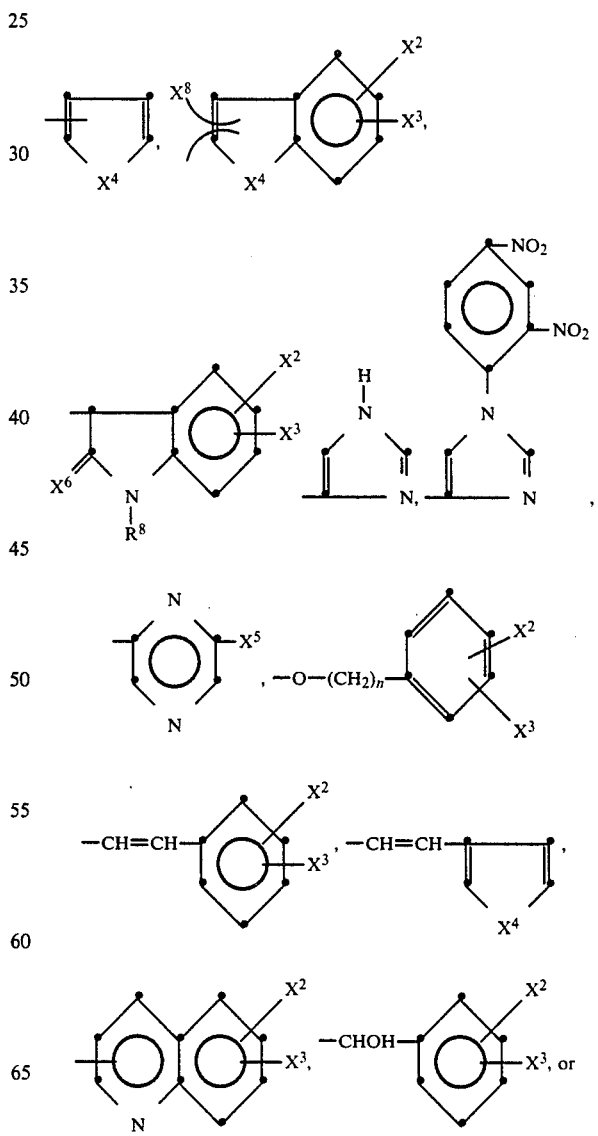

-continued

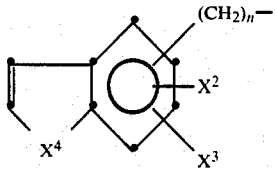

(with the proviso that q is not 0 or 1 in —(CH$_2$)$_n$NH(CH$_2$)$_q$R$^7$ and that q is not 0 in

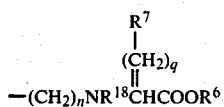

when R$^7$ or R$_a^7$ is

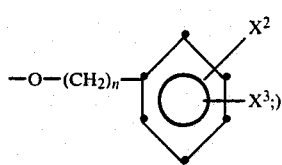

R$^8$ is H, loweralkyl, cyclololoweralkyl, —(CH$_2$)$_m$CONH$_2$, —(CH$_2$)$_m$COOR$^6$, —(CH$_2$)$_n$-cyclolow-eralkyl, —(CH$_2$)$_m$NR$^4$R$^5$,

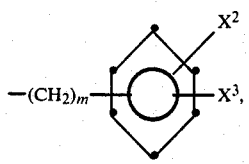

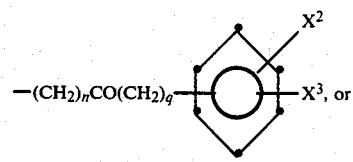

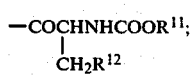

R$^9$ and R$^{10}$ are independently H, —OH, or —CH$_3$;
R$^{11}$ and R$^{12}$ are independently loweralkyl or cyclo-loweralkyl;
R$^{13}$ is H, loweralkyl, acyl, O, or cyclololoweralkyl;
R$^{14}$ is loweralkyl or phenylloweralkyl;
R$^{18}$ is H, loweralkyl, or acyl;
m is 1–4;
n is 0–4;
p is 0 when its adjacent === is unsaturated and 1 when its adjacent === is saturated, except that when R$^{13}$ is O, P=1 and === is unsaturated;
q is 0–4;
r is 1 or 2;
X$^1$ is H, —NO$_2$, CF$_3$CN, OH, loweralkyl, halo, loweralkylthio, loweralkoxy, —(CH$_2$)$_n$COOR$^6$, —NR$^4$R$^5$, or

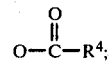

X$^2$ and X$^3$ are independently H, —OH, —NO$_2$, halo, loweralkylthio, loweralkyl, loweralkoxy or

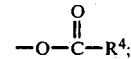

X$^4$ is S, O, CH$_2$, or NR$^8$;
X$^5$ is H, CF$_3$, CN, —COOR$^6$, NO$_2$, or halo;
X$^6$ is O or HH;
X$^8$ is H or loweralkyl;
X$^9$ and X$_a^9$ are independently NR$^{18}$, O;
X$^{10}$ is F, Cl, Br;
=== is a saturated or unsaturated bond
and the pharmaceutically acceptable salts thereof.

As used herein, the definition of each expression, e.g., m, n, p, loweralkyl, etc., when it occurs more than once in any structure, is intended to be independent of its definition elsewhere in the same structure. Thus, the ring fragment

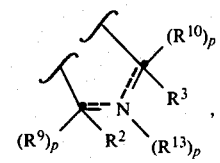

since each p is independently 1 or 0, represents the three structures

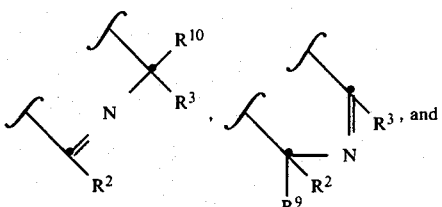

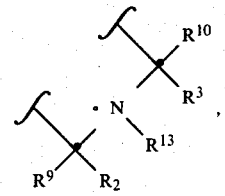

when R$^{13}$ is not O.

In the compounds of Formula I, the preferred stereochemistry relates to D-tryptophan, where C$^{3a}$ and N$^5$ of Formula I correspond to the carbonyl carbon and α-amino nitrogen of D-tryptophan and R$^3$ occupies the position of the indolylmethyl side chain.

As used herein, halo is F, Cl, Br, or I; loweralkyl is 1–4 carbon straight or branched chain alkyl and includes methyl, ethyl, propyl, isopropyl, butyl, isobutyl, and t-butyl; in loweralkoxy and loweralkylthio, the alkyl portion is loweralkyl as previously defined; cycloloweralkyl is cycloalkyl of 3–5 carbons; loweralkenyl is 1–5 carbon straight or branched chain alkenyl; and acyl is formyl, acetyl, propionyl, or butyryl.*

*Loweralkynyl is also 1–5 carbon straight or branched chain alkynyl.

The pharmaceutically acceptable salts of the compounds of Formulas I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, p-aminobenzoic, p-acetamidobenzoic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

The pharmaceutically acceptable salts of the acid of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

An embodiment of this invention is the preparation of compounds of Formula I.

Another embodiment is the use of the compounds of Formula I for the treatment and the prevention of disorders of the gastrointestinal, central nervous, and appetite regulatory systems of mammals, especially of man. Specifically, the Formula I compounds are useful in treatment and prevention of disorders of gastric acid secretion, gastrointestinal motility, pancreatic secretions, and dopaminergic functions. The compounds of Formula I are especially useful in the prevention and treatment of irritable bowel syndrome.

A further embodiment is a composition comprising an effective amount of a compound of Formula I and a pharmaceutically acceptable carrier.

The ability of the compounds of Formula I to antagonize CCK and gastrin makes these compounds useful as pharmaceutical agents. These compounds will be especially useful in the treatment and prevention of disease states wherein CCK or gastrin may be involved, for example, gastrointestinal disorders such as irritable bowel syndrome, ulcers, excess pancreatic or gastric secretion, acute pancreatitis, motility disorders, pain (potentiation of opiate analgesia), central nervous system disorders caused by CCK's interaction with dopamine such as neuroleptic disorders, tardive dyskinesia, Parkinson's disease, psychosis or Gilles de la Tourette Syndrome, disorders of appetite regulatory systems, Zollinger-Ellison syndrome, and antral G. cell hyperplasia.

The compounds of Formula I or pharmaceutically acceptable salts thereof, can be administered to a human subject either alone, or preferably, in combination with pharmaceutically acceptable carriers or diluents, in a pharmaceutical composition, according to standard pharmaceutical practice. The compounds can be administered orally or parenterally. Parenteral administration includes intravenous, intramuscular, intraperitoneal, subcutaneous and topical administration.

For oral use of an antagonist of CCK or gastrin of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of Formula I or a salt thereof is used as an antagonist of CCK or gastrin in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range from about 0.05 mg to about 50 mg/kg and preferably 0.5 mg to about 20 mg/kg in a single or divided doses. On the other hand, it may be necessary to use dosages outside these limits in some cases.

The compounds of Formula I are prepared according to the following schemes.

REACTION SCHEME I
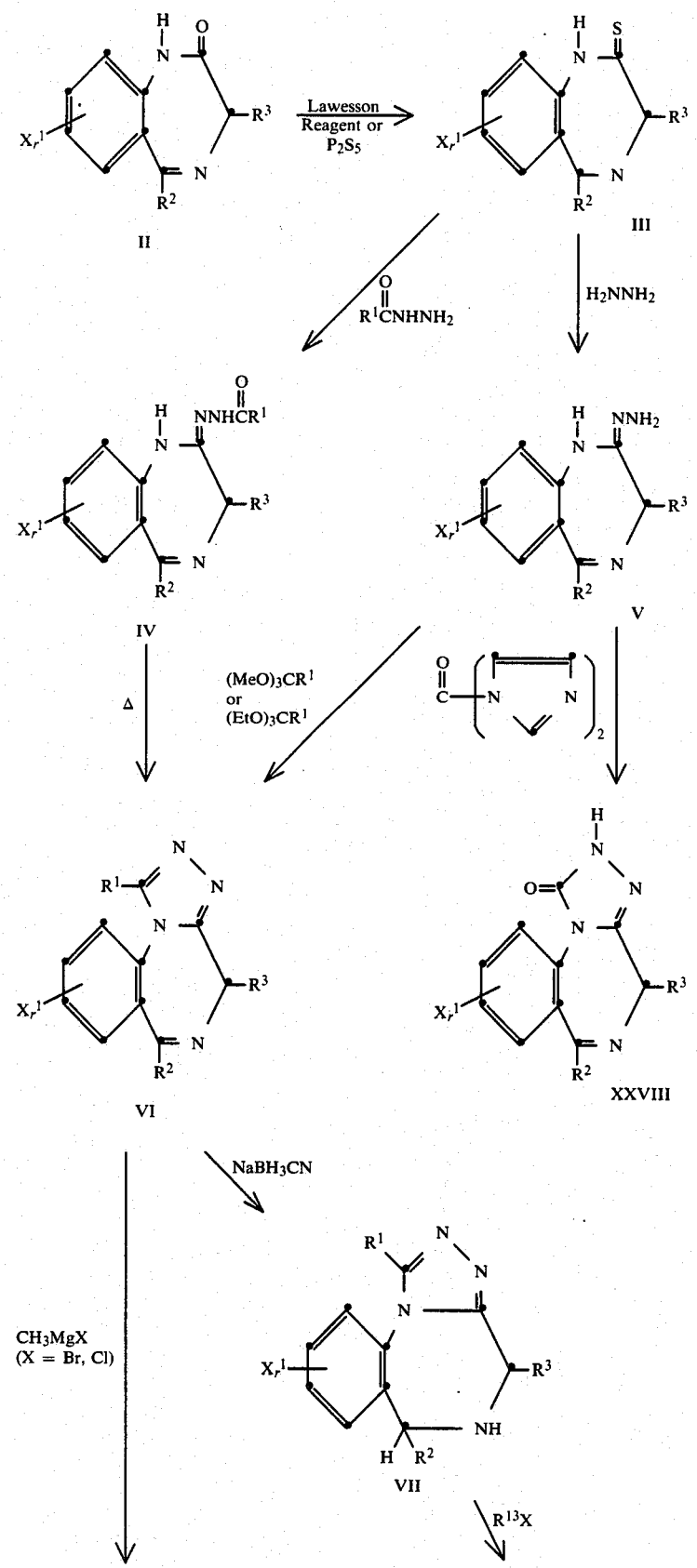

REACTION SCHEME I
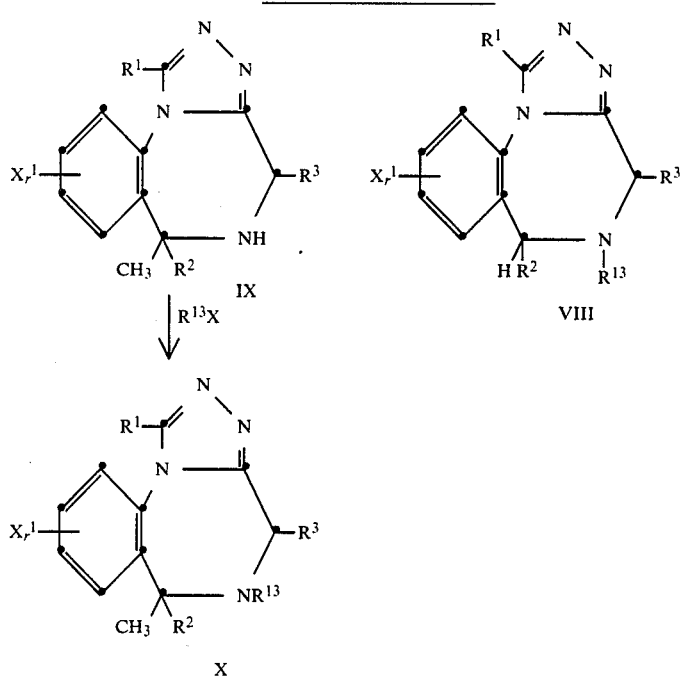
REACTION SCHEME II
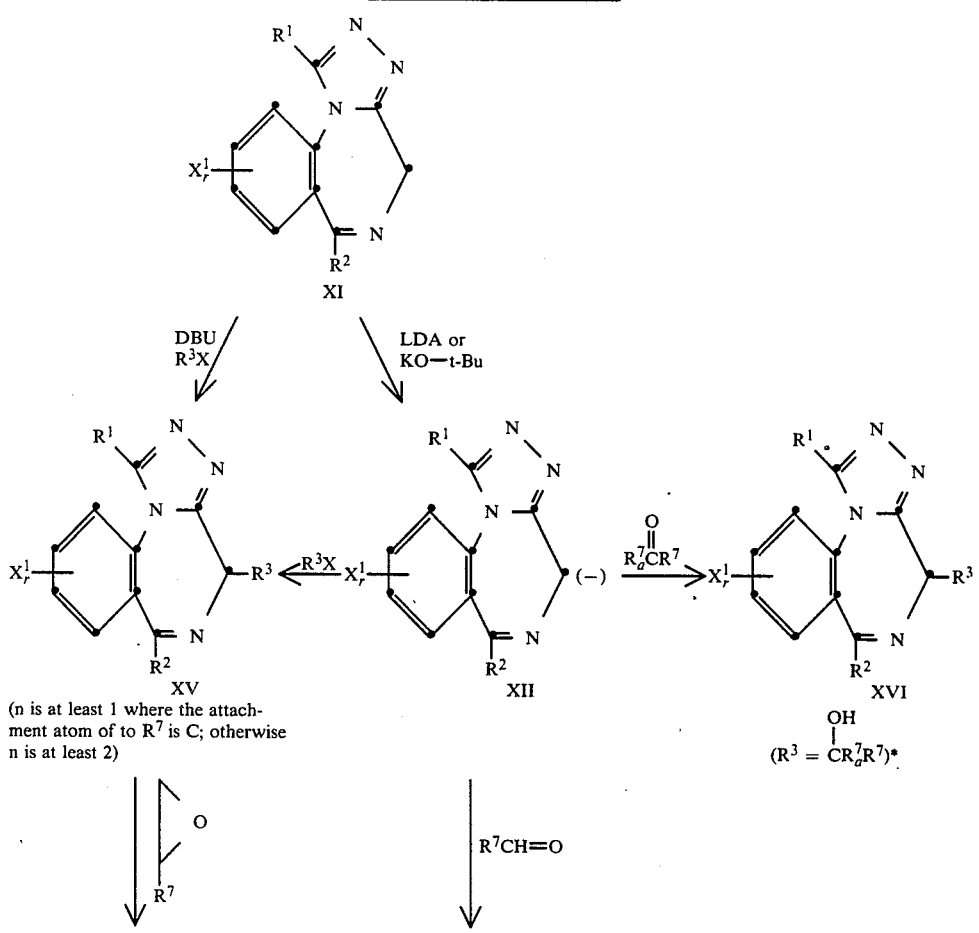

-continued
REACTION SCHEME II

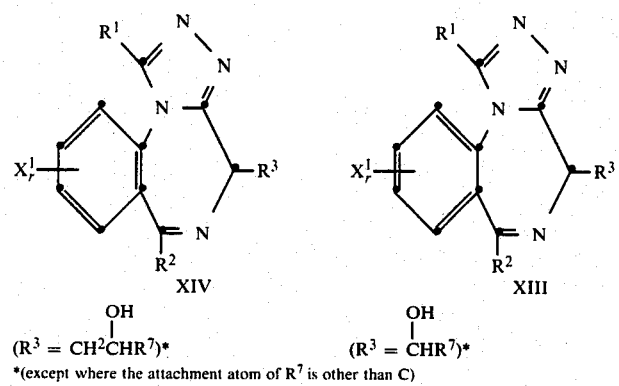

XIV  (R³ = CH²CHR⁷)*

XIII  (R³ = CHR⁷)*

*(except where the attachment atom of R⁷ is other than C)

REACTION SCHEME III

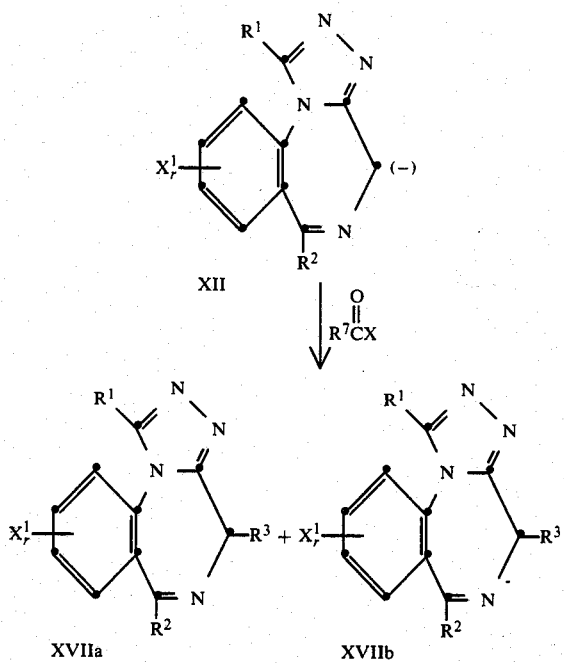

XII

XVIIa    XVIIb

-continued
REACTION SCHEME III or (if peroxide present)

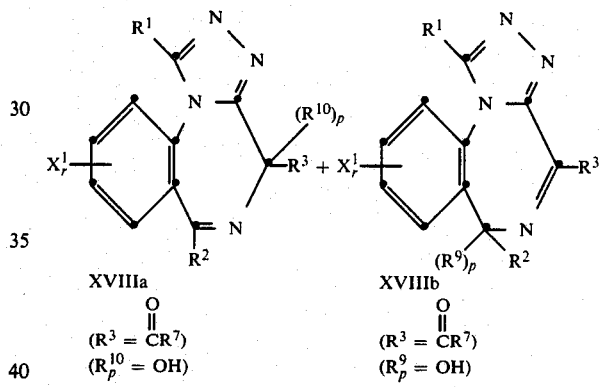

XVIIIa
($R^3 = CR^7$ with =O)
($R^{10}_p = OH$)

XVIIIb
($R^3 = CR^7$ with =O)
($R^9_p = OH$)

(except where atom adjacent to R⁷ is other than C)

REACTION SCHEME IV

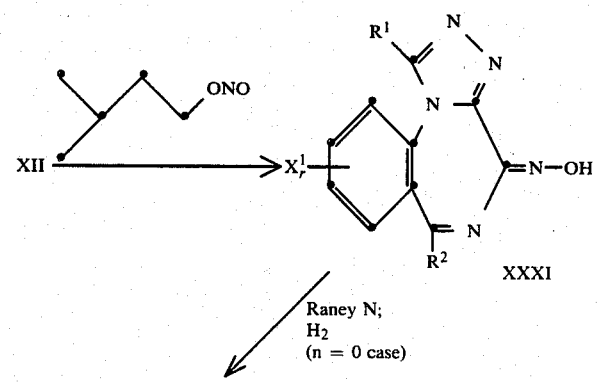

XII → XXXI

Raney N;
H₂
(n = 0 case)

-continued
REACTION SCHEME IV
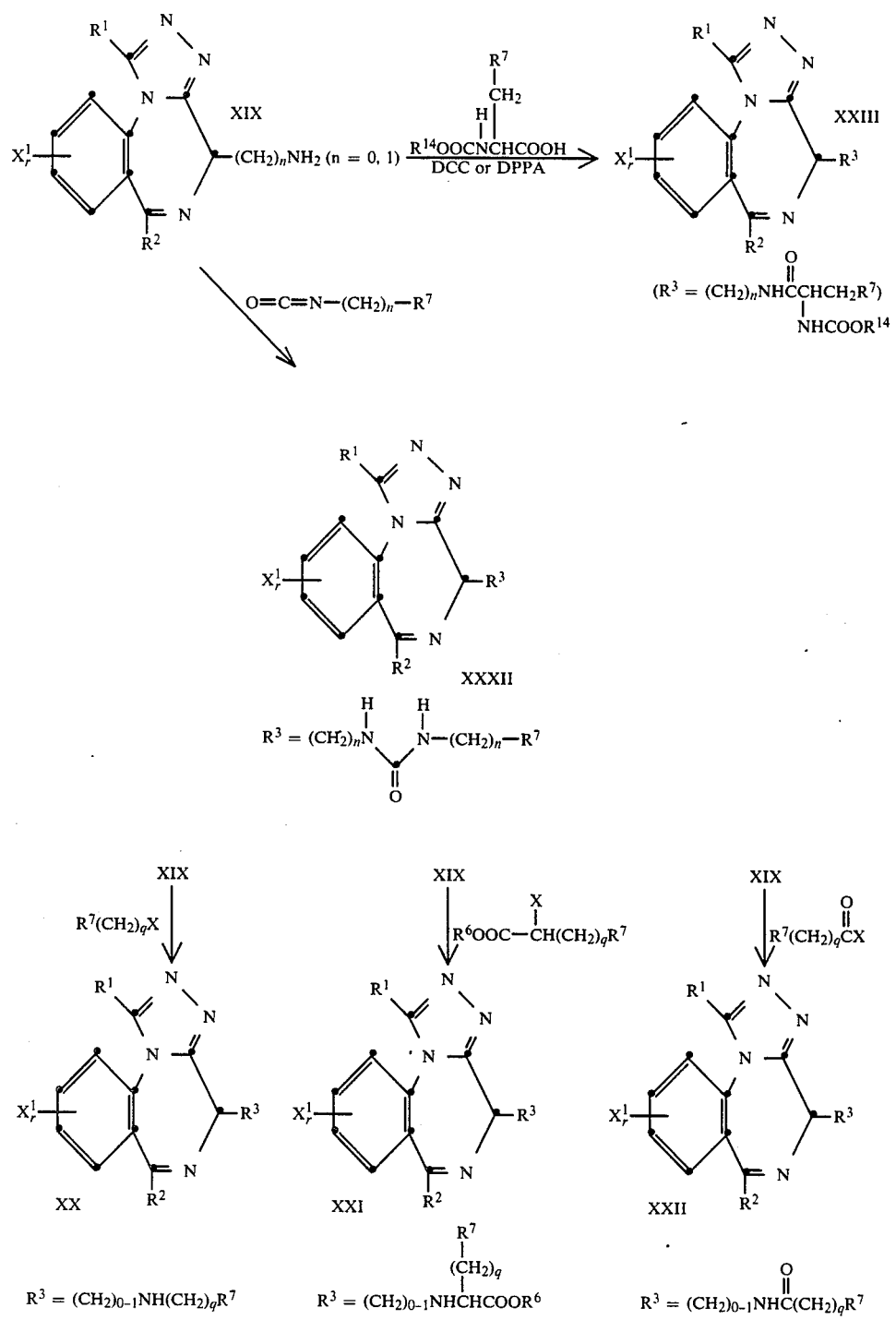

REACTION SCHEME V
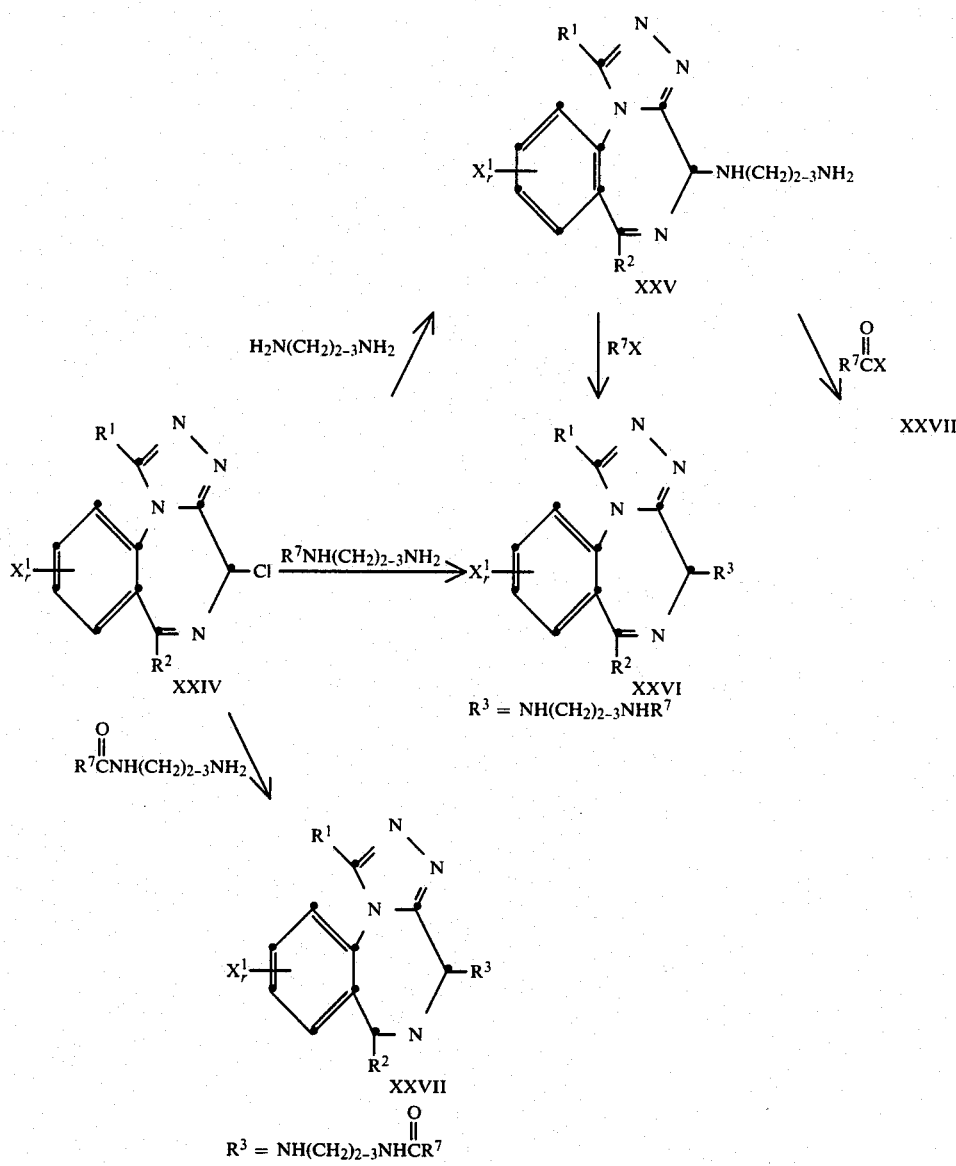
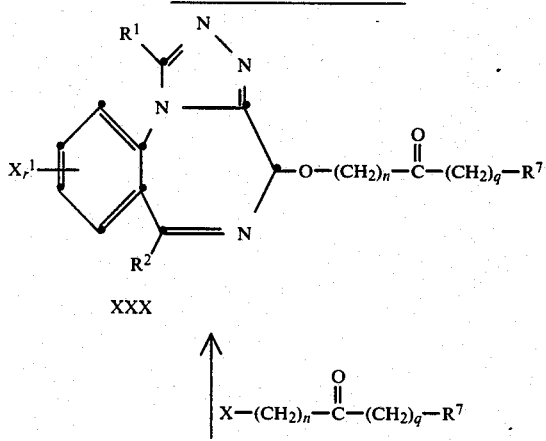
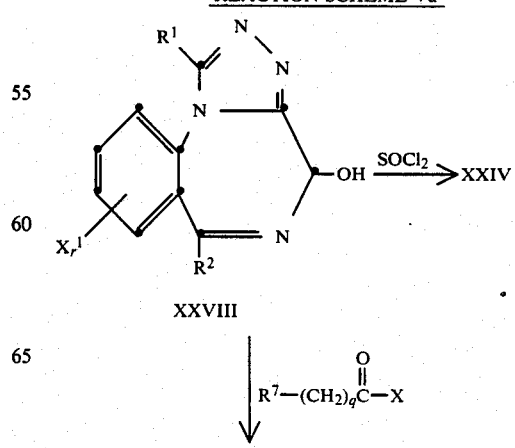

-continued
REACTION SCHEME Va

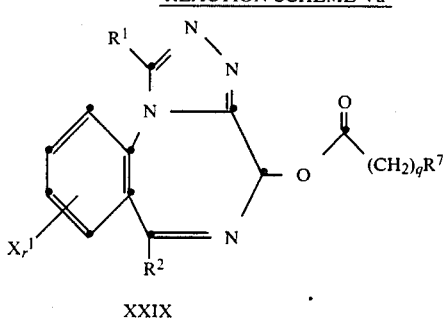

XXIX

Referring to Reaction Scheme I, the benzodiazepinones of Formula II are reacted with Lawesson's reagent

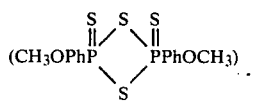

in an organic solvent and heated at reflux in an inert atmosphere. Upon cooling, the reaction mixture is separated, as by silica gel chromatography, to produce the benzodiazepinethione (III).

The triazolobenzodiazepines (VI) can be generated from III by either (1) reacting III with hydrazine to produce the benzodiazepinehydrazone (V) which is then combined with a trialkyllorthoester at acidic pH, or (2) reacting III with an acylhydrazide in a heated organic solvent or produce the acylamidrazone IV which is then heated to produce VI. Compound V is also converted to XXVIII by treatment with carbonyldiimidazole.

VI is stirred in acetic acid at 10° C. and treated with sodium cyanoborohydride. The mixture is stirred from 5 to 60 minutes, preferably 5 minutes, and the reaction monitored by thin layer chromatography (tlc). The mixture is diluted with cold water, made basic and extracted with organic solvents. The organic layers are combined, washed with brine, dried over sodium sulfate, filtered, and evaporated to dryness in vacuo and the residue is purified by column chromatography on silica gel or by recrystallization to give 5,6-dihydrobenzodiazepines VII.

The compound VII in methylene chloride is treated with an excess of an acyl halide or anhydride, e.g. benzoyl chloride or acetic anhydride, or an alkyl halide, e.g. methyl iodide or ethyl bromide, and stirred at room temperature. With acyl halides or anhydrides, a base such as triethyl amine or 4-dimethylaminopyridine is added as a catalyst. Upon completion of the reaction (1-92 hrs), the mixture is diluted with water and separated. The organic layer is washed with water, sodium carbonate, dried filtered, and evaporated. The residue is purified by recrystallization or by column chromatography on silica gel to give 5-alkyl- and 5-acyl-5,6-dihydro-4H-s-triazolo [4,3-a]-1,4-benzodiazepines, VIII.

Alternatively, IV is treated with a Grignard reagent to yield the amine IX which is then reacted analogously to VII to yield the N-alkyl or N-acyl analog X.

Referring now to Reaction Scheme II, the anion XII is generated from XI by the procedure of J. Org. Chem., 46, 3945 (1981) using lithium diisopropylamide (LDA) or using potassium tert-butoxide.

XII can be variously treated. For example, the hydroxy alkyl derivative XIII is generated by adding an aldehyde to a solution of XII. Treatment of XII with an epoxide yields the hydroxyethyl derivative XIV. By treating XII with an alkyl halide, the alkyl derivative XV is produced. Lastly, the hydroxy alkyl compoun XVI is derived from treatment of XII with a ketone.

An alternative procedure for obtaining XV is to treat XI with an alkyl halide and a strong base such as 1,8-diazabicyclo[5.4.0]undec-7-ene (DBU) and heating.

These procedures also produce isomers of XIII-XVI which are analogous to XVIIb (Reaction Scheme III). Likewise, in the presence of peroxide, the analogs of the isomers and hydroxy derivatives XVIIIa and XVIIIb are produced.

Reaction Scheme III describes the formation of $R^3$=keto compounds of Formula I. These are produced by treating the anion XII with an acid halide or anhydride. This reaction produces both isomers XVIIa and XVIIb. When the reaction is run in the presence of peroxide, the hydroxy compounds XVIIIa and XVIIIb are produced.

Reaction Scheme IV describes the formation of Formula I compounds where $R^3$ is a substituted amino or aminomethyl.

The triazolobenzodiazepines XIX are either known or readily derivable from known compounds. The former compound may also be obtained by nitrosation of XII followed by reduction of the oxime XXXI with Raney nickel and hydrogen.

When XIX is trtreated with an alkyl halide, the N-alkyl derivative XX is produced.

When XIX is treated with an alpha-halo carboxylic acid derivative such as an α-halo acid, ester, amide, or the like, one obtains the corresponding α-amino compound XXI.

Treatment of XIX with an acid halide or anhydride produces the N-acyl derivative XXII.

Compound XIX may also be treated with an N-protected α-amino acid and a coupling reagent such as DCC or DPPA (diphenylphosphorylazide) to give the amides of structure XXIII.

Treatment of Compound XIX with an isocyanate gives the ureas XXXII.

Referring now to Reaction Schemes V/Va, the 4-hydroxy-triazolobenzo diazepine (XXVIII) is treated with thionyl chloride to give the 4-chloro-triazolobenzodiazepine XXIV. The chloride is treated with an excess amount of ethylene or propylene diamine to yield the substituted diamine XXV. XXV can be reacted with an alkyl halide to yield the alkyl derivative XXVI. XXVI can also be directly derived from XXIV by treatment of XXIV with a monoalkyl ethylene or propylene diamine. The hydroxy compound (XXVIII) may also be either acylated or alkylated to give (XXVIII) and (XXX) respectively.

Treatment of XXIV with an acid halide or anhydride produces the N-acyl diamine XXVII, which can also be directly produced from XXIV by treatment of XXIV with a monoacyl ethylene or propylene diamine.

In cases where the starting materials are optically active, the chirality at $C_4$ is controlled by the synthesis. When racemic starting materials are employed, racemic products are obtained. The enantiomers may be separated by resolution.

In Vitro Activity of Formula I

The biological activity of the compounds of Formula I have been evaluated using (1) an $^{125}$I-CCK receptor binding assay and in vitro isolated tissue preparations and (2) $^{125}$I-gastrin and $^3$H-pentagastrin binding assays.

MATERIALS AND METHODS

1. CCK receptor binding (pancreas)

CCK-33 was radiolabeled with $^{125}$I-Bolton Hunter reagent (2000 Ci/mmole) as described by Sankara et al. (*J. Biol. Chem.* 254: 9349-9351, 1979). Receptor binding was performed according to Innis and Snyder (*Proc. Natl. Acad. Sci.* 77: 6917-6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200-350 g) were sacrificed by decapitation. The whole pancreas was dissected free of fat tissue and was homogenized in 20 volumes of ice-cold 50 mM. Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 µl of buffer (for total binding) or unlabeled CCK-8 sulfate to give a final concentration of 1 µM (for nonspecific binding) or the compounds of Formula I (for determination of inhibition of $^{125}$I-CCK binding) and 25 µl of $^{125}$I-CCK-33 (30,000-40,000 cpm) were added to 450 µl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (*Ann. N.Y. Acad. Sci.* 51: 660, 1949), $^{125}$I-CCK-33 was progressively diluted with increasing concentrations of CCK-33.

2. CCK Receptor Binding (Brain)

CCK-33 was radiolabeled and the binding was performed according to the description for the pancreas method with modification according to Saito et al. (*J. Neurochem.* 37, 483-490, 1981).

Male Hartley guinea pigs (300-500 g) were sacrificed by decapitation and the brains were removed and placed in ice-cold 50 mM. Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris Trizma buffer with a Brinkman polytron PT-10. The homogenates were centrifuged at 42,000 g for 15 min. Pellets were resuspended in Tris Buffer, centrifuged as above and resuspended in 200 volumes of binding assay buuffer (10 mM N-2-hydroxyethyl-piperazine-N'-2-ethane sulfonic acid (HEPES), 5 mM MgCl$_2$, 0.25 mg/ml bacitracin, 1 mM ethylene glycol-bis-(β-aminoethylether-N,N'-tetra-acetic acid (EGTA), and 0.4% bovine serum albumin (BSA)). For the binding assay, 25 µl of buffer (for total binding) or unlabeled CCK-8 sulfate to give a final concentration of 1 µM (for nonspecific binding) or the compounds of Formula I (for determination of inhibition of $^{125}$I-CCK binding) and 25 µl of $^{125}$I-CCK-33 (30,000-40,000 cpm) were added to 450 µl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400-600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, KH$_2$PO$_4$ 1.19 mM, MgSO$_4$ 1.2 mM, NaHCO$_3$ 25 mM and dextrose 11 mM) maintained at 32° C. and bubbled with 95% O$_2$ and 5% CO$_2$. Isometric contractions are recorded using Statham (60 g; 0.12 mm) strain gauges and a Hewlett-Packard (77588) recorder. The tissues are washed every 10 minutes for 1 hr to obtain equilibrium prior to the beginning of the study. CCK-8 is added cumulatively to the baths and EC$_{50}$'s determined using regression analysis. After washout (every 10 minutes for 1 hr), the compound of Formula I is added at least 5 minutes before the addition of CCK-8 and the EC$_{50}$ of CCK-8 in the presence of the compound of Formula I similarly determined.

4. Isolated longitudinal muscle of guinea pig ileum

Longitudinal muscle strips with attached nerve plexus are prepared as described in *Brit J. Pharmac.* 23: 356-363, 1964; *J. Physiol.* 194: 13-33, 1969. Male Hartley guinea pigs are decapitated and the ileum is removed (10 cm of the terminal ileum is discarded and the adjacent 20 cm piece is used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% O$_2$ and 5% CO$_2$ at 37° C. under 0.5 g tension. CCK-8 is added cumulatively to the baths and EC$_{50}$ values in the presence and absence of compounds of Formula I determined as described in the gall bladder protocol (above).

GASTRIN ANTAGONISM

Gastrin antagonist activity of compounds of Formula I is determined using the following assay:

GASTRIN RECEPTOR BINDING IN GUINEA PIG GASTRIC GLANDS PREPARATION OF QUINEA PIG GASTRIC MUCOSAL GLANDS

Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300-500 g body weight, male Hartley) were washed thoroughly and minced with fine scissors in standard buffer consisting of the following: 130 mM NaCl, 12 mM NaHCO$_3$, 3 mM NaH$_2$PO$_4$, 3 mM Na$_2$HPO$_4$, 3 mM K$_2$HPO$_4$, 2 mM MgSO4, 1 mM CaCl2, 5 mM glucose and 4 mM L-glutamine, 25 mM HEPES at pH 7.4. The minced tissues were washed and then incubated in a 37° C. shaker bath for 40 minutes with the buuffer containing 0.1% collagenase and 0.1% BSA and bubbled with 95% O2 and 5% CO2. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

BINDING STUDIES

The washed guinea pig gastric glands prepared as above were resuspended in 25 ml of standard buffer containing 0.25 mg/ml of bacitracin. For binding studies, to 220 μl of gastric glands in triplicate tubes, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) were added. The tubes were aerated with 95% O2 and 5% CO2 and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}$I-gastrin or liquid scintillation counting for $^3$H-pentagastrin.

Representative Formula I compounds were assayed and found to have gastrin inhibiting activity.

IN VITRO RESULTS

1. Effect of the Compounds of Formula I on $^{125}$I-CCK-33 Receptor Binding

The preferred compounds of Formula I inhibited specific $^{125}$I-CCK-33 binding in a concentration dependent manner.

Scatchard analysis of specific $^{125}$I-CCK-33 receptor binding in the absence and presence of the compounds of Formula I indicated the compounds of Formula I competitively inhibited specific $^{125}$I-CCK-33 receptor binding since it increased the $K_D$ (dissociation constant) without affecting the $B_{max}$ (maximum receptor number). A $K_i$ value (dissociation constant of inhibitor) of the compounds of Formula I was estimated.

The data of Table 1 were obtained for compounds of the following formula:

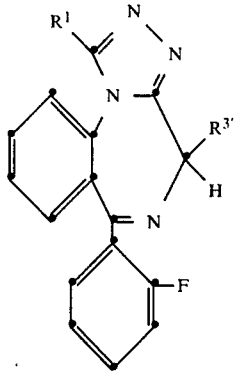

Formula IA

| Compound No. | $R^1$ | $R^{3'}$ |
|---|---|---|
| 1 | H | —CH2—indol-3-yl |
| 2 | CH3 | —CH2—indol-3-yl |
| 3 | phenyl | —CH2—indol-3-yl |
| 4 | —CH2—N(CH3)2 | —CH2—indol-3-yl |
| 5 | OH | —CH2—indol-3-yl |
| 6 | CCl3 | —CH2—indol-3-yl |
| 7 | H | —NH—CO—OCH2—phenyl |
| 8 | H | —NH—CO—4-chlorophenyl |
| 9 | H | —NH—CO—indol-2-yl |
| 10 | CH3 | —NH—CO—indol-2-yl |

TABLE 1

| | CCK Receptor Binding Results | |
|---|---|---|
| | IC50(μM) | |
| Formula IA Compound No. | $^{125}$I-CCK Pancreas | $^{125}$I-CCK Brain |
| 1 | 0.2 | 100 |
| 2 | 0.3 | 38.6 |
| 3 | 22 | 100 |
| 4 | 14 | 100 |
| 5 | 3.1 | 63 |
| 6 | 25 | >100 |
| 7 | 0.22 | 8 |
| 8 | 0.0044 | 9.3 |
| 9 | 0.0009 | 0.053 |
| 10 | 0.0004 | 0.066 |

Preferred compounds of Formula I are those of the series where $R^1$ is H, methyl, carboxyl, carboxyethyl, carboxymethyl, or trifluoromethyl.

Other series of preferred compounds are those where $R^2$ is phenyl, p-chlorophenyl, o-fluorophenyl, o-chlorophenyl, p-fluorophenyl, 2,4-dichlorophenyl, 2,6-difluorophenyl, —CH2COO—t—butyl, or —CH2COOEt.

Other series of preferred compounds are those where $R^3$ is 2- or 3-indolylmethyl, CO—2-(1-methyl-indolyl), CO—3-(1-methyl-indolyl), —CO—thiophene, —CHOH—1-methylindol-3-yl, NHCONH—p-Cl-phenyl, NHCO—$R^7$ where $R^7$ is 2-indolyl, 2-(1-methylindolyl), 2-(5-F-indolyl), -2-benzofuranyl, -2-benzothienyl, -2-(3-methylindenyl), phenylethenyl, mono- or dihalo phenyl, mono- or dimethyl or trifluoromethyl phenyl.

When p is 1 for any of $R^9$, $R^{10}$ or $R^{13}$, it is preferred that $R^9$ is H or hydroxyl, $R^{10}$ is H or hydroxyl, and $R^{13}$ is H.

It is preferred that $X_r^1$ is H, Cl, F, CF3, OH; or NO2.

Examples off Formula I compounds are tabulated below.

TABLE 2

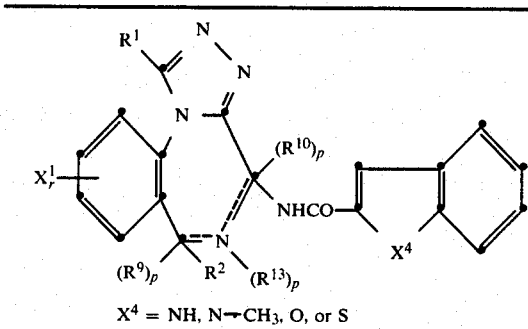

$X^4$ = NH, N—$CH_3$, O, or S

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 3

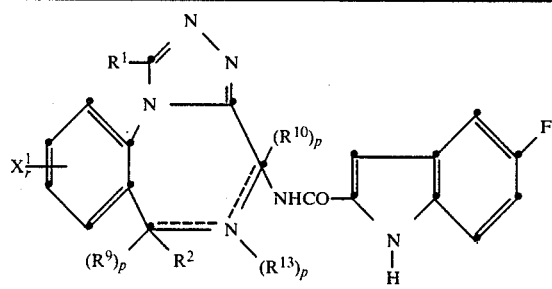

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |

TABLE 3-continued

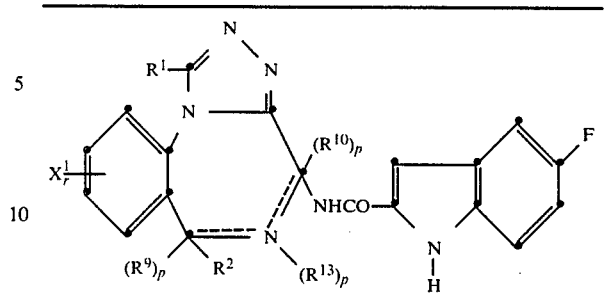

| $X^1$ | r | $R^1$ | $(R^9)_p$ | $R^2$ | $(R^{13})_p$ | $(R^{10})_p$ |
|---|---|---|---|---|---|---|
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

TABLE 4

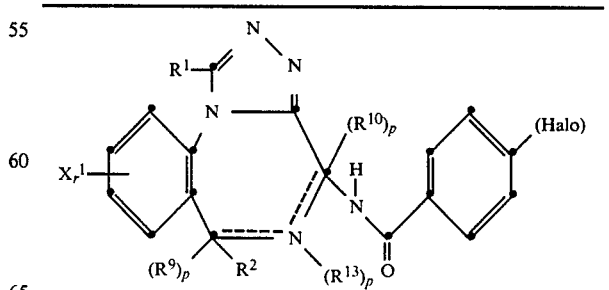

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |

TABLE 4-continued

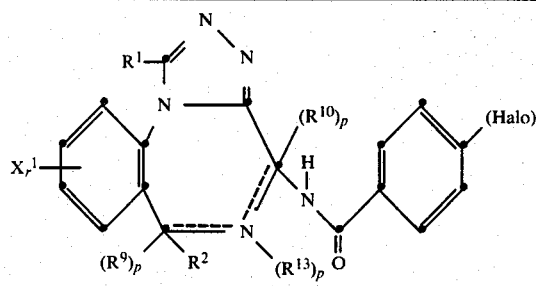

| X¹ | r | R¹ | (R⁹)$_p$ | R² | (R¹³)$_p$ | (R¹⁰)$_p$ |
|---|---|---|---|---|---|---|
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt—Bu | — | H |
| Cl | 1 | H | — | CH₂COOt—Bu | — | H |
| F | 1 | H | — | CH₂COOt—Bu | — | H |
| CF₃ | 1 | H | — | CH₂COOt—Bu | — | H |
| OH | 1 | H | — | CH₂COOt—Bu | — | H |
| NO₂ | 1 | H | — | CH₂COOt—Bu | — | H |

TABLE 4-continued

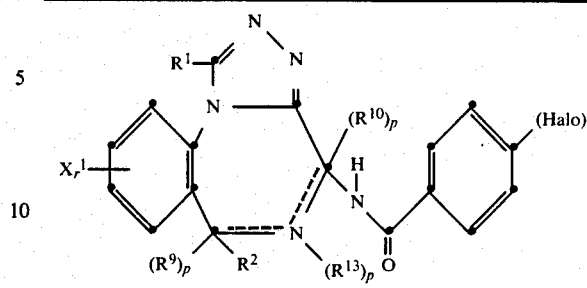

| X¹ | r | R¹ | (R⁹)$_p$ | R² | (R¹³)$_p$ | (R¹⁰)$_p$ |
|---|---|---|---|---|---|---|
| H | 1 | CH₃ | — | CH₂COOt—Bu | — | H |
| Cl | 1 | CH₃ | — | CH₂COOt—Bu | — | H |
| F | 1 | CH₃ | — | CH₂COOt—Bu | — | H |
| CF₃ | 1 | CH₃ | — | CH₂COOt—Bu | — | H |
| OH | 1 | CH₃ | — | CH₂COOt—Bu | — | H |
| NO₂ | 1 | CH₃ | — | CH₂COOt—Bu | — | H |
| H | 1 | COOH | — | CH₂COOt—Bu | — | H |
| Cl | 1 | COOH | — | CH₂COOt—Bu | — | H |
| F | 1 | COOH | — | CH₂COOt—Bu | — | H |
| CF₃ | 1 | COOH | — | CH₂COOt—Bu | — | H |
| OH | 1 | COOH | — | CH₂COOt—Bu | — | H |
| NO₂ | 1 | COOH | — | CH₂COOt—Bu | — | H |
| H | 1 | CF₃ | — | CH₂COOt—Bu | — | H |
| OH | 1 | CF₃ | — | CH₂COOt—Bu | — | H |
| H | 1 | CH₂COOH | — | CH₂COOt—Bu | — | H |
| OH | 1 | CH₂COOH | — | CH₂COOt—Bu | — | H |
| H | 1 | CH₂CH₂COOH | — | CH₂COOt—Bu | — | H |
| OH | 1 | CH₂CH₂COOH | — | CH₂COOt—Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 5

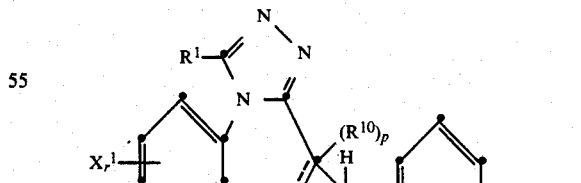

| X¹ | r | R¹ | (R⁹)$_p$ | R² | (R¹³)$_p$ | (R¹⁰)$_p$ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |

TABLE 5-continued

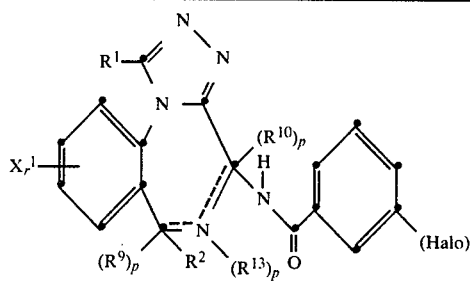

| X¹ | r | R¹ | (R⁹)p | R² | (R¹³)p | (R¹⁰)p |
|---|---|---|---|---|---|---|
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 6

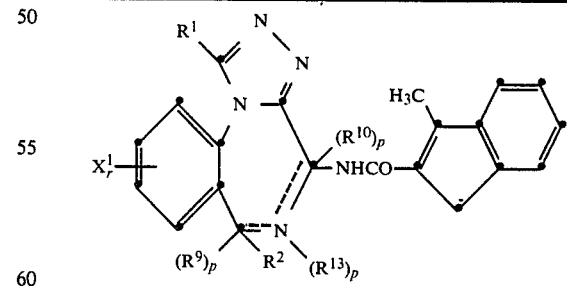

| X¹ | r | R¹ | (R⁹)p | R² | (R¹³)p | (R¹⁰)p |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |

TABLE 6-continued

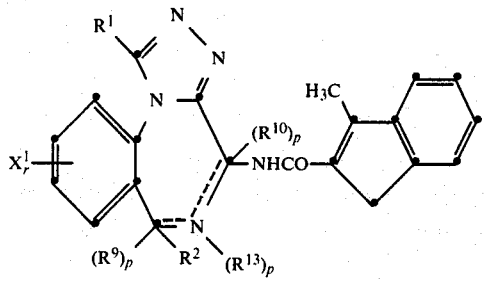

| X¹ | r | R¹ | (R⁹)ₚ | R² | (R¹³)ₚ | (R¹⁰)ₚ |
|---|---|---|---|---|---|---|
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |

TABLE 6-continued

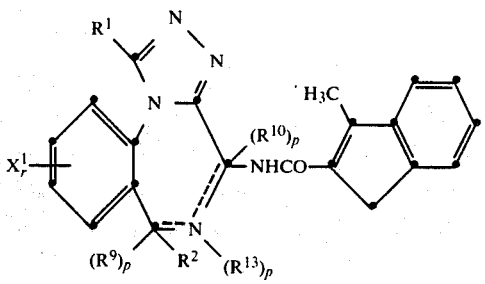

| X¹ | r | R¹ | (R⁹)ₚ | R² | (R¹³)ₚ | (R¹⁰)ₚ |
|---|---|---|---|---|---|---|
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 7

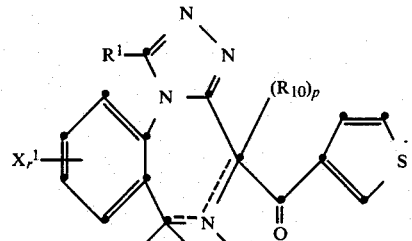

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |

TABLE 7-continued

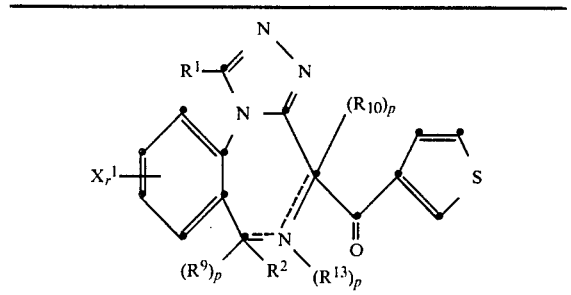

| $X^1$ | r | $R^1$ | $(R^9)_p$ | $R^2$ | $(R^{13})_p$ | $(R^{10})_p$ |
|---|---|---|---|---|---|---|
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph. | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |

TABLE 7-continued

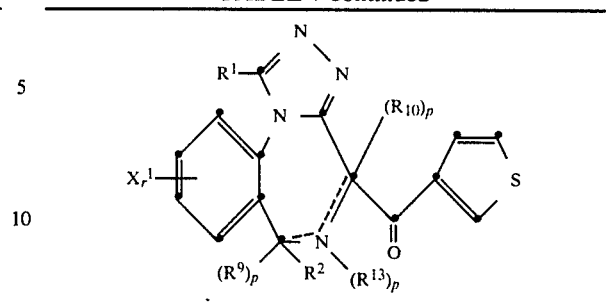

| $X^1$ | r | $R^1$ | $(R^9)_p$ | $R^2$ | $(R^{13})_p$ | $(R^{10})_p$ |
|---|---|---|---|---|---|---|
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |
| H | 1 | $CH_3$ | — | Ph | — | OH |
| H | 1 | $CF_3$ | — | Ph | — | OH |
| H | 1 | COOH | — | Ph | — | OH |
| H | 1 | $CH_3$ | — | o-F—Ph | — | OH |
| H | 1 | $CF_3$ | — | o-F—Ph | — | OH |
| H | 1 | COOH | — | o-F—Ph | — | OH |
| H | 1 | $CH_3$ | — | $CH_2COOt$-Bu | — | OH |
| H | 1 | $CF_3$ | — | $CH_2COOt$-Bu | — | OH |
| H | 1 | COOH | — | $CH_2COOt$-Bu | — | OH |

TABLE 8

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |

TABLE 8-continued

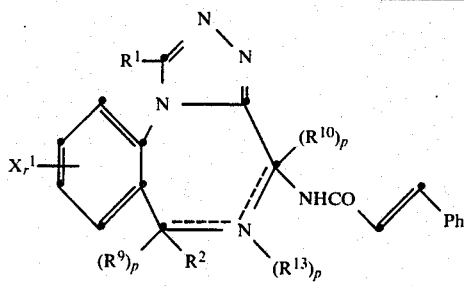

| X¹ | r | R¹ | (R⁹)ₚ | R² | (R¹³)ₚ | (R¹⁰)ₚ |
|---|---|---|---|---|---|---|
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt—Bu | — | H |
| Cl | 1 | H | — | CH₂COOt—Bu | — | H |
| F | 1 | H | — | CH₂COOt—Bu | — | H |
| CF₃ | 1 | H | — | CH₂COOt—Bu | — | H |
| OH | 1 | H | — | CH₂COOt—Bu | — | H |
| NO₂ | 1 | H | — | CH₂COOt—Bu | — | H |
| H | 1 | CH₃ | — | CH₂COOt—Bu | — | H |
| Cl | 1 | CH₃ | — | CH₂COOt—Bu | — | H |
| F | 1 | CH₃ | — | CH₂COOt—Bu | — | H |
| CF₃ | 1 | CH₃ | — | CH₂COOt—Bu | — | H |
| OH | 1 | CH₃ | — | CH₂COOt—Bu | — | H |
| NO₂ | 1 | CH₃ | — | CH₂COOt—Bu | — | H |
| H | 1 | COOH | — | CH₂COOt—Bu | — | H |
| Cl | 1 | COOH | — | CH₂COOt—Bu | — | H |
| F | 1 | COOH | — | CH₂COOt—Bu | — | H |
| CF₃ | 1 | COOH | — | CH₂COOt—Bu | — | H |
| OH | 1 | COOH | — | CH₂COOt—Bu | — | H |
| NO₂ | 1 | COOH | — | CH₂COOt—Bu | — | H |
| H | 1 | CF₃ | — | CH₂COOt—Bu | — | H |
| OH | 1 | CF₃ | — | CH₂COOt—Bu | — | H |
| H | 1 | CH₂COOH | — | CH₂COOt—Bu | — | H |
| OH | 1 | CH₂COOH | — | CH₂COOt—Bu | — | H |
| H | 1 | CH₂CH₂COOH | — | CH₂COOt—Bu | — | H |
| OH | 1 | CH₂CH₂COOH | — | CH₂COOt—Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 9

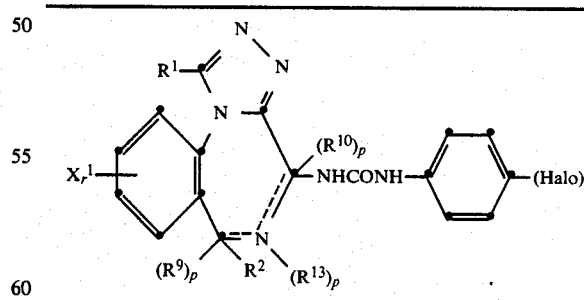

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |

TABLE 9-continued

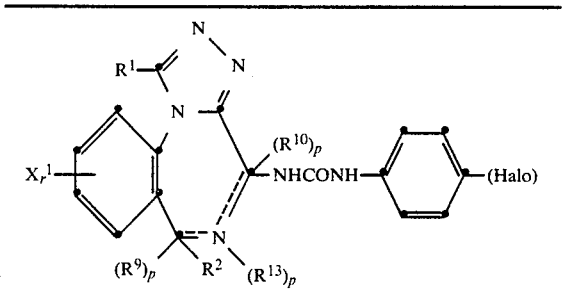

| X¹ | r | R¹ | (R⁹)ₚ | R² | (R¹³)ₚ | (R¹⁰)ₚ |
|---|---|---|---|---|---|---|
| F | 1 | CH₃ | — | Ph | — | H |
| CF₃ | 1 | CH₃ | — | Ph | — | H |
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |

TABLE 9-continued

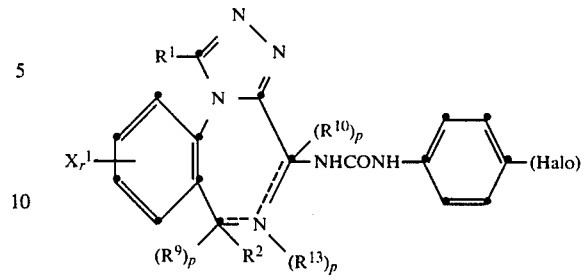

| X¹ | r | R¹ | (R⁹)ₚ | R² | (R¹³)ₚ | (R¹⁰)ₚ |
|---|---|---|---|---|---|---|
| H | 1 | COOH | — | CH₂COOt-Bu | — | H |
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |

TABLE 10

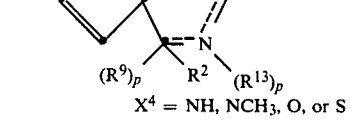

X⁴ = NH, NCH₃, O, or S

| X¹ | r | R¹ | (R⁹)ₚ | R² | (R¹³)ₚ | (R¹⁰)ₚ |
|---|---|---|---|---|---|---|
| H | 1 | H | — | Ph | — | H |
| Cl | 1 | H | — | Ph | — | H |
| F | 1 | H | — | Ph | — | H |
| CF₃ | 1 | H | — | Ph | — | H |
| OH | 1 | H | — | Ph | — | H |
| NO₂ | 1 | H | — | Ph | — | H |
| H | 1 | CH₃ | — | Ph | — | H |
| Cl | 1 | CH₃ | — | Ph | — | H |
| F | 1 | CH₃ | — | Ph | — | H |
| CF₃ | 1 | CH₃ | — | Ph | — | H |

TABLE 10-continued

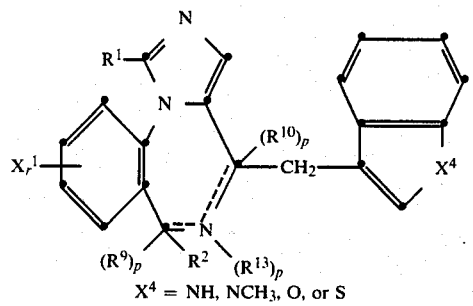

$X^4 = NH, NCH_3, O, or S$

| $X^1$ | r | $R^1$ | $(R^9)_p$ | $R^2$ | $(R^{13})_p$ | $(R^{10})_p$ |
|---|---|---|---|---|---|---|
| OH | 1 | CH₃ | — | Ph | — | H |
| NO₂ | 1 | CH₃ | — | Ph | — | H |
| H | 1 | COOH | — | Ph | — | H |
| Cl | 1 | COOH | — | Ph | — | H |
| F | 1 | COOH | — | Ph | — | H |
| CF₃ | 1 | COOH | — | Ph | — | H |
| OH | 1 | COOH | — | Ph | — | H |
| NO₂ | 1 | COOH | — | Ph | — | H |
| H | 1 | CF₃ | — | Ph | — | H |
| OH | 1 | CF₃ | — | Ph | — | H |
| H | 1 | CH₂COOH | — | Ph | — | H |
| OH | 1 | CH₂COOH | — | Ph | — | H |
| H | 1 | CH₂CH₂COOH | — | Ph | — | H |
| OH | 1 | CH₂CH₂COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF₃ | 1 | H | — | o-F—Ph | — | H |
| OH | 1 | H | — | o-F—Ph | — | H |
| NO₂ | 1 | H | — | o-F—Ph | — | H |
| H | 1 | CH₃ | — | o-F—Ph | — | H |
| Cl | 1 | CH₃ | — | o-F—Ph | — | H |
| F | 1 | CH₃ | — | o-F—Ph | — | H |
| CF₃ | 1 | CH₃ | — | o-F—Ph | — | H |
| OH | 1 | CH₃ | — | o-F—Ph | — | H |
| NO₂ | 1 | CH₃ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF₃ | 1 | COOH | — | o-F—Ph | — | H |
| OH | 1 | COOH | — | o-F—Ph | — | H |
| NO₂ | 1 | COOH | — | o-F—Ph | — | H |
| H | 1 | CF₃ | — | o-F—Ph | — | H |
| OH | 1 | CF₃ | — | o-F—Ph | — | H |
| H | 1 | CH₂COOH | — | o-F—Ph | — | H |
| OH | 1 | CH₂COOH | — | o-F—Ph | — | H |
| H | 1 | CH₂CH₂COOH | — | o-F—Ph | — | H |
| OH | 1 | CH₂CH₂COOH | — | o-F—Ph | — | H |
| H | 1 | H | — | p-Cl—Ph | — | H |
| F | 1 | H | — | p-Cl—Ph | — | H |
| CF₃ | 1 | H | — | p-Cl—Ph | — | H |
| OH | 1 | H | — | p-Cl—Ph | — | H |
| H | 1 | CH₃ | — | p-Cl—Ph | — | H |
| F | 1 | CH₃ | — | p-Cl—Ph | — | H |
| CF₃ | 1 | CH₃ | — | p-Cl—Ph | — | H |
| OH | 1 | CH₃ | — | p-Cl—Ph | — | H |
| H | 1 | COOH | — | p-Cl—Ph | — | H |
| F | 1 | COOH | — | p-Cl—Ph | — | H |
| CF₃ | 1 | COOH | — | p-Cl—Ph | — | H |
| OH | 1 | COOH | — | p-Cl—Ph | — | H |
| H | 1 | CF₃ | — | p-Cl—Ph | — | H |
| H | 1 | CH₂COOH | — | p-Cl—Ph | — | H |
| H | 1 | CH₂CH₂COOH | — | p-Cl—Ph | — | H |
| H | 1 | H | — | CH₂COOt-Bu | — | H |
| Cl | 1 | H | — | CH₂COOt-Bu | — | H |
| F | 1 | H | — | CH₂COOt-Bu | — | H |
| CF₃ | 1 | H | — | CH₂COOt-Bu | — | H |
| OH | 1 | H | — | CH₂COOt-Bu | — | H |
| NO₂ | 1 | H | — | CH₂COOt-Bu | — | H |
| H | 1 | CH₃ | — | CH₂COOt-Bu | — | H |
| Cl | 1 | CH₃ | — | CH₂COOt-Bu | — | H |
| F | 1 | CH₃ | — | CH₂COOt-Bu | — | H |
| CF₃ | 1 | CH₃ | — | CH₂COOt-Bu | — | H |
| OH | 1 | CH₃ | — | CH₂COOt-Bu | — | H |
| NO₂ | 1 | CH₃ | — | CH₂COOt-Bu | — | H |
| H | 1 | COOH | — | CH₂COOt-Bu | — | H |

TABLE 10-continued

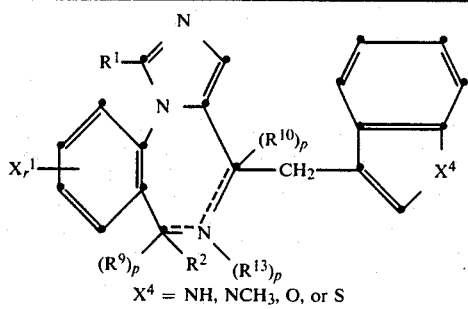

$X^4 = NH, NCH_3, O, or S$

| $X^1$ | r | $R^1$ | $(R^9)_p$ | $R^2$ | $(R^{13})_p$ | $(R^{10})_p$ |
|---|---|---|---|---|---|---|
| Cl | 1 | COOH | — | CH₂COOt-Bu | — | H |
| F | 1 | COOH | — | CH₂COOt-Bu | — | H |
| CF₃ | 1 | COOH | — | CH₂COOt-Bu | — | H |
| OH | 1 | COOH | — | CH₂COOt-Bu | — | H |
| NO₂ | 1 | COOH | — | CH₂COOt-Bu | — | H |
| H | 1 | CF₃ | — | CH₂COOt-Bu | — | H |
| OH | 1 | CF₃ | — | CH₂COOt-Bu | — | H |
| H | 1 | CH₂COOH | — | CH₂COOt-Bu | — | H |
| OH | 1 | CH₂COOH | — | CH₂COOt-Bu | — | H |
| H | 1 | CH₂CH₂COOH | — | CH₂COOt-Bu | — | H |
| OH | 1 | CH₂CH₂COOH | — | CH₂COOt-Bu | — | H |
| H | 1 | H | — | CH₂COOEt | — | H |
| Cl | 1 | H | — | CH₂COOEt | — | H |
| F | 1 | H | — | CH₂COOEt | — | H |
| CF₃ | 1 | H | — | CH₂COOEt | — | H |
| OH | 1 | H | — | CH₂COOEt | — | H |
| NO₂ | 1 | H | — | CH₂COOEt | — | H |
| H | 1 | CH₃ | — | CH₂COOEt | — | H |
| Cl | 1 | CH₃ | — | CH₂COOEt | — | H |
| F | 1 | CH₃ | — | CH₂COOEt | — | H |
| CF₃ | 1 | CH₃ | — | CH₂COOEt | — | H |
| OH | 1 | CH₃ | — | CH₂COOEt | — | H |
| NO₂ | 1 | CH₃ | — | CH₂COOEt | — | H |
| H | 1 | COOH | — | CH₂COOEt | — | H |
| Cl | 1 | COOH | — | CH₂COOEt | — | H |
| F | 1 | COOH | — | CH₂COOEt | — | H |
| CF₃ | 1 | COOH | — | CH₂COOEt | — | H |
| OH | 1 | COOH | — | CH₂COOEt | — | H |
| NO₂ | 1 | COOH | — | CH₂COOEt | — | H |
| H | 1 | CF₃ | — | CH₂COOEt | — | H |
| OH | 1 | CF₃ | — | CH₂COOEt | — | H |
| H | 1 | CH₂COOH | — | CH₂COOEt | — | H |
| OH | 1 | CH₂COOH | — | CH₂COOEt | — | H |
| H | 1 | CH₂CH₂COOH | — | CH₂COOEt | — | H |
| OH | 1 | CH₂CH₂COOH | — | CH₂COOEt | — | H |
| H | 1 | CH₃ | — | Ph | — | OH |
| H | 1 | CF₃ | — | Ph | — | OH |
| H | 1 | COOH | — | Ph | — | OH |
| H | 1 | CH₃ | — | o-F—Ph | — | OH |
| H | 1 | CF₃ | — | o-F—Ph | — | OH |
| H | 1 | COOH | — | o-F—Ph | — | OH |
| H | 1 | CH₃ | — | CH₂COOt-Bu | — | OH |
| H | 1 | CF₃ | — | CH₂COOt-Bu | — | OH |
| H | 1 | COOH | — | CH₂COOt-Bu | — | OH |

TABLE 11

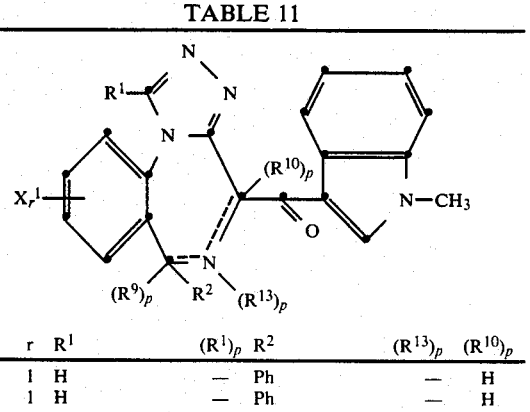

| $X^1$ | r | $R^1$ | $(R^1)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |

TABLE 11-continued

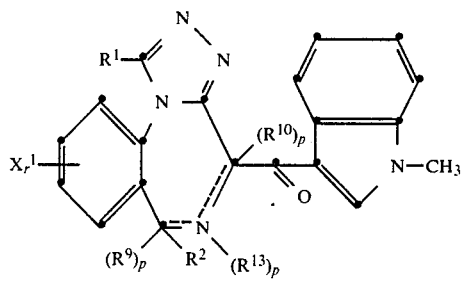

| $X^1$ | r | $R^1$ | $(R^1)_p$ | $R^2$ | $(R^{13})_p$ | $(R^{10})_p$ |
|---|---|---|---|---|---|---|
| F | 1 | H | — | Ph | — | H |
| CF$_3$ | 1 | H | — | Ph | — | H |
| OH | 1 | H | — | Ph | — | H |
| NO$_2$ | 1 | H | — | Ph | — | H |
| H | 1 | CH$_3$ | — | Ph | — | H |
| Cl | 1 | CH$_3$ | — | Ph | — | H |
| F | 1 | CH$_3$ | — | Ph | — | H |
| CF$_3$ | 1 | CH$_3$ | — | Ph | — | H |
| OH | 1 | CH$_3$ | — | Ph | — | H |
| NO$_2$ | 1 | CH$_3$ | — | Ph | — | H |
| H | 1 | COOH | — | Ph | — | H |
| Cl | 1 | COOH | — | Ph | — | H |
| F | 1 | COOH | — | Ph | — | H |
| CF$_3$ | 1 | COOH | — | Ph | — | H |
| OH | 1 | COOH | — | Ph | — | H |
| NO$_2$ | 1 | COOH | — | Ph | — | H |
| H | 1 | CF$_3$ | — | Ph | — | H |
| OH | 1 | CF$_3$ | — | Ph | — | H |
| H | 1 | CH$_2$COOH | — | Ph | — | H |
| OH | 1 | CH$_2$COOH | — | Ph | — | H |
| H | 1 | CH$_2$CH$_2$COOH | — | Ph | — | H |
| OH | 1 | CH$_2$CH$_2$COOH | — | Ph | — | H |
| H | 1 | H | — | o-F—Ph | — | H |
| Cl | 1 | H | — | o-F—Ph | — | H |
| F | 1 | H | — | o-F—Ph | — | H |
| CF$_3$ | 1 | H | — | o-F—Ph | — | H |
| OH | 1 | H | — | o-F—Ph | — | H |
| NO$_2$ | 1 | H | — | o-F—Ph | — | H |
| H | 1 | CH$_3$ | — | o-F—Ph | — | H |
| Cl | 1 | CH$_3$ | — | o-F—Ph | — | H |
| F | 1 | CH$_3$ | — | o-F—Ph | — | H |
| CF$_3$ | 1 | CH$_3$ | — | o-F—Ph | — | H |
| OH | 1 | CH$_3$ | — | o-F—Ph | — | H |
| NO$_2$ | 1 | CH$_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| CF$_3$ | 1 | COOH | — | o-F—Ph | — | H |
| OH | 1 | COOH | — | o-F—Ph | — | H |
| NO$_2$ | 1 | COOH | — | o-F—Ph | — | H |
| H | 1 | CF$_3$ | — | o-F—Ph | — | H |
| OH | 1 | CF$_3$ | — | o-F—Ph | — | H |
| H | 1 | CH$_2$COOH | — | o-F—Ph | — | H |
| OH | 1 | CH$_2$COOH | — | o-F—Ph | — | H |
| H | 1 | CH$_2$CH$_2$COOH | — | o-F—Ph | — | H |
| OH | 1 | CH$_2$CH$_2$COOH | — | o-F—Ph | — | H |
| H | 1 | H | — | p-Cl—Ph | — | H |
| F | 1 | H | — | p-Cl—Ph | — | H |
| CF$_3$ | 1 | H | — | p-Cl—Ph | — | H |
| OH | 1 | H | — | p-Cl—Ph | — | H |
| H | 1 | CH$_3$ | — | p-Cl—Ph | — | H |
| F | 1 | CH$_3$ | — | p-Cl—Ph | — | H |
| CF$_3$ | 1 | CH$_3$ | — | p-Cl—Ph | — | H |
| OH | 1 | CH$_3$ | — | p-Cl—Ph | — | H |
| H | 1 | COOH | — | p-Cl—Ph | — | H |
| F | 1 | COOH | — | p-Cl—Ph | — | H |
| CF$_3$ | 1 | COOH | — | p-Cl—Ph | — | H |
| OH | 1 | COOH | — | p-Cl—Ph | — | H |
| H | 1 | CF$_3$ | — | p-Cl—Ph | — | H |
| H | 1 | CH$_2$COOH | — | p-Cl—Ph | — | H |
| H | 1 | CH$_2$CH$_2$COOH | — | p-Cl—Ph | — | H |
| H | 1 | H | — | CH$_2$COOt—Bu | — | H |
| Cl | 1 | H | — | CH$_2$COOt—Bu | — | H |
| F | 1 | H | — | CH$_2$COOt—Bu | — | H |
| CF$_3$ | 1 | H | — | CH$_2$COOt—Bu | — | H |
| OH | 1 | H | — | CH$_2$COOt—Bu | — | H |
| NO$_2$ | 1 | H | — | CH$_2$COOt—Bu | — | H |
| H | 1 | CH$_3$ | — | CH$_2$COOt—Bu | — | H |
| Cl | 1 | CH$_3$ | — | CH$_2$COOt—Bu | — | H |
| F | 1 | CH$_3$ | — | CH$_2$COOt—Bu | — | H |
| CF$_3$ | 1 | CH$_3$ | — | CH$_2$COOt—Bu | — | H |
| OH | 1 | CH$_3$ | — | CH$_2$COOt—Bu | — | H |
| NO$_2$ | 1 | CH$_3$ | — | CH$_2$COOt—Bu | — | H |
| H | 1 | COOH | — | CH$_2$COOt—Bu | — | H |
| Cl | 1 | COOH | — | CH$_2$COOt—Bu | — | H |
| F | 1 | COOH | — | CH$_2$COOt—Bu | — | H |
| CF$_3$ | 1 | COOH | — | CH$_2$COOt—Bu | — | H |
| OH | 1 | COOH | — | CH$_2$COOt—Bu | — | H |
| NO$_2$ | 1 | COOH | — | CH$_2$COOt—Bu | — | H |
| H | 1 | CF$_3$ | — | CH$_2$COOt—Bu | — | H |
| OH | 1 | CF$_3$ | — | CH$_2$COOt—Bu | — | H |
| H | 1 | CH$_2$COOH | — | CH$_2$COOt—Bu | — | H |
| OH | 1 | CH$_2$COOH | — | CH$_2$COOt—Bu | — | H |
| H | 1 | CH$_2$CH$_2$COOH | — | CH$_2$COOt—Bu | — | H |
| OH | 1 | CH$_2$CH$_2$COOH | — | CH$_2$COOt—Bu | — | H |
| H | 1 | H | — | CH$_2$COOEt | — | H |
| Cl | 1 | H | — | CH$_2$COOEt | — | H |
| F | 1 | H | — | CH$_2$COOEt | — | H |
| CF$_3$ | 1 | H | — | CH$_2$COOEt | — | H |
| OH | 1 | H | — | CH$_2$COOEt | — | H |
| NO$_2$ | 1 | H | — | CH$_2$COOEt | — | H |
| H | 1 | CH$_3$ | — | CH$_2$COOEt | — | H |
| Cl | 1 | CH$_3$ | — | CH$_2$COOEt | — | H |
| F | 1 | CH$_3$ | — | CH$_2$COOEt | — | H |
| CF$_3$ | 1 | CH$_3$ | — | CH$_2$COOEt | — | H |
| OH | 1 | CH$_3$ | — | CH$_2$COOEt | — | H |
| NO$_2$ | 1 | CH$_3$ | — | CH$_2$COOEt | — | H |
| H | 1 | COOH | — | CH$_2$COOEt | — | H |
| Cl | 1 | COOH | — | CH$_2$COOEt | — | H |
| F | 1 | COOH | — | CH$_2$COOEt | — | H |
| CF$_3$ | 1 | COOH | — | CH$_2$COOEt | — | H |
| OH | 1 | COOH | — | CH$_2$COOEt | — | H |
| NO$_2$ | 1 | COOH | — | CH$_2$COOEt | — | H |
| H | 1 | CF$_3$ | — | CH$_2$COOEt | — | H |
| OH | 1 | CF$_3$ | — | CH$_2$COOEt | — | H |
| H | 1 | CH$_2$COOH | — | CH$_2$COOEt | — | H |
| OH | 1 | CH$_2$COOH | — | CH$_2$COOEt | — | H |
| H | 1 | CH$_2$CH$_2$COOH | — | CH$_2$COOEt | — | H |
| OH | 1 | CH$_2$CH$_2$COOH | — | CH$_2$COOEt | — | H |
| H | 1 | CH$_3$ | — | Ph | — | OH |
| H | 1 | CF$_3$ | — | Ph | — | OH |
| H | 1 | COOH | — | Ph | — | OH |
| H | 1 | CH$_3$ | — | o-F—Ph | — | OH |
| H | 1 | CF$_3$ | — | o-F—Ph | — | OH |
| H | 1 | COOH | — | o-F—Ph | — | OH |
| H | 1 | CH$_3$ | — | CH$_2$COOt—Bu | — | OH |
| H | 1 | CF$_3$ | — | CH$_2$COOt—Bu | — | OH |
| H | 1 | COOH | — | CH$_2$COOt—Bu | — | OH |

TABLE 12

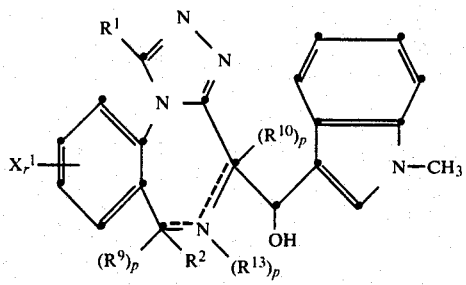

| $X^1$ | r | $R^1$ | $(R^9)_p$ | $R^2$ | $(R^{13})_p$ | $(R^{10})_p$ |
|---|---|---|---|---|---|---|
| H | 1 | H | — | Ph | — | H |
| Cl | 1 | H | — | Ph | — | H |
| F | 1 | H | — | Ph | — | H |
| $CF_3$ | 1 | H | — | Ph | — | H |
| OH | 1 | H | — | Ph | — | H |
| $NO_2$ | 1 | H | — | Ph | — | H |
| H | 1 | $CH_3$ | — | Ph | — | H |
| Cl | 1 | $CH_3$ | — | Ph | — | H |
| F | 1 | $CH_3$ | — | Ph | — | H |
| $CF_3$ | 1 | $CH_3$ | — | Ph | — | H |
| OH | 1 | $CH_3$ | — | Ph | — | H |
| $NO_2$ | 1 | $CH_3$ | — | Ph | — | H |
| H | 1 | COOH | — | Ph | — | H |
| Cl | 1 | COOH | — | Ph | — | H |
| F | 1 | COOH | — | Ph | — | H |
| $CF_3$ | 1 | COOH | — | Ph | — | H |
| OH | 1 | COOH | — | Ph | — | H |
| $NO_2$ | 1 | COOH | — | Ph | — | H |
| H | 1 | $CF_3$ | — | Ph | — | H |
| OH | 1 | $CF_3$ | — | Ph | — | H |
| H | 1 | $CH_2COOH$ | — | Ph | — | H |
| OH | 1 | $CH_2COOH$ | — | Ph | — | H |
| H | 1 | $CH_2CH_2COOH$ | — | Ph | — | H |
| OH | 1 | $CH_2CH_2COOH$ | — | Ph | — | H |
| H | 1 | H | — | o-F—Ph | — | H |
| Cl | 1 | H | — | o-F—Ph | — | H |
| F | 1 | H | — | o-F—Ph | — | H |
| $CF_3$ | 1 | H | — | o-F—Ph | — | H |
| OH | 1 | H | — | o-F—Ph | — | H |
| $NO_2$ | 1 | H | — | o-F—Ph | — | H |
| H | 1 | $CH_3$ | — | o-F—Ph | — | H |
| Cl | 1 | $CH_3$ | — | o-F—Ph | — | H |
| F | 1 | $CH_3$ | — | o-F—Ph | — | H |
| $CF_3$ | 1 | $CH_3$ | — | o-F—Ph | — | H |
| OH | 1 | $CH_3$ | — | o-F—Ph | — | H |
| $NO_2$ | 1 | $CH_3$ | — | o-F—Ph | — | H |
| H | 1 | COOH | — | o-F—Ph | — | H |
| Cl | 1 | COOH | — | o-F—Ph | — | H |
| F | 1 | COOH | — | o-F—Ph | — | H |
| $CF_3$ | 1 | COOH | — | o-F—Ph | — | H |
| OH | 1 | COOH | — | o-F—Ph | — | H |
| $NO_2$ | 1 | COOH | — | o-F—Ph | — | H |
| H | 1 | $CF_3$ | — | o-F—Ph | — | H |
| OH | 1 | $CF_3$ | — | o-F—Ph | — | H |
| H | 1 | $CH_2COOH$ | — | o-F—Ph | — | H |
| OH | 1 | $CH_2COOH$ | — | o-F—Ph | — | H |
| H | 1 | $CH_2CH_2COOH$ | — | o-F—Ph | — | H |
| OH | 1 | $CH_2CH_2COOH$ | — | o-F—Ph | — | H |
| H | 1 | H | — | p-Cl—Ph | — | H |
| F | 1 | H | — | p-Cl—Ph | — | H |
| $CF_3$ | 1 | H | — | p-Cl—Ph | — | H |
| OH | 1 | H | — | p-Cl—Ph | — | H |
| H | 1 | $CH_3$ | — | p-Cl—Ph | — | H |
| F | 1 | $CH_3$ | — | p-Cl—Ph | — | H |
| $CF_3$ | 1 | $CH_3$ | — | p-Cl—Ph | — | H |
| OH | 1 | $CH_3$ | — | p-Cl—Ph | — | H |
| H | 1 | COOH | — | p-Cl—Ph | — | H |
| F | 1 | COOH | — | p-Cl—Ph | — | H |
| $CF_3$ | 1 | COOH | — | p-Cl—Ph | — | H |
| OH | 1 | COOH | — | p-Cl—Ph | — | H |
| H | 1 | $CF_3$ | — | p-Cl—Ph | — | H |
| H | 1 | $CH_2COOH$ | — | p-Cl—Ph | — | H |
| H | 1 | $CH_2CH_2COOH$ | — | p-Cl—Ph | — | H |
| H | 1 | H | — | $CH_2COOt$-Bu | — | H |
| Cl | 1 | H | — | $CH_2COOt$-Bu | — | H |
| F | 1 | H | — | $CH_2COOt$-Bu | — | H |
| $CF_3$ | 1 | H | — | $CH_2COOt$-Bu | — | H |
| OH | 1 | H | — | $CH_2COOt$-Bu | — | H |
| $NO_2$ | 1 | H | — | $CH_2COOt$-Bu | — | H |
| H | 1 | $CH_3$ | — | $CH_2COOt$-Bu | — | H |
| Cl | 1 | $CH_3$ | — | $CH_2COOt$-Bu | — | H |
| F | 1 | $CH_3$ | — | $CH_2COOt$-Bu | — | H |
| $CF_3$ | 1 | $CH_3$ | — | $CH_2COOt$-Bu | — | H |
| OH | 1 | $CH_3$ | — | $CH_2COOt$-Bu | — | H |
| $NO_2$ | 1 | $CH_3$ | — | $CH_2COOt$-Bu | — | H |
| H | 1 | COOH | — | $CH_2COOt$-Bu | — | H |
| Cl | 1 | COOH | — | $CH_2COOt$-Bu | — | H |
| F | 1 | COOH | — | $CH_2COOt$-Bu | — | H |
| $CF_3$ | 1 | COOH | — | $CH_2COOt$-Bu | — | H |
| OH | 1 | COOH | — | $CH_2COOt$-Bu | — | H |
| $NO_2$ | 1 | COOH | — | $CH_2COOt$-Bu | — | H |
| H | 1 | $CF_3$ | — | $CH_2COOt$-Bu | — | H |
| OH | 1 | $CF_3$ | — | $CH_2COOt$-Bu | — | H |
| H | 1 | $CH_2COOH$ | — | $CH_2COOt$-Bu | — | H |
| OH | 1 | $CH_2COOH$ | — | $CH_2COOt$-Bu | — | H |
| H | 1 | $CH_2CH_2COOH$ | — | $CH_2COOt$-Bu | — | H |
| OH | 1 | $CH_2CH_2COOH$ | — | $CH_2COOt$-Bu | — | H |
| H | 1 | H | — | $CH_2COOEt$ | — | H |
| Cl | 1 | H | — | $CH_2COOEt$ | — | H |
| F | 1 | H | — | $CH_2COOEt$ | — | H |
| $CF_3$ | 1 | H | — | $CH_2COOEt$ | — | H |
| OH | 1 | H | — | $CH_2COOEt$ | — | H |
| $NO_2$ | 1 | H | — | $CH_2COOEt$ | — | H |
| H | 1 | $CH_3$ | — | $CH_2COOEt$ | — | H |
| Cl | 1 | $CH_3$ | — | $CH_2COOEt$ | — | H |
| F | 1 | $CH_3$ | — | $CH_2COOEt$ | — | H |
| $CF_3$ | 1 | $CH_3$ | — | $CH_2COOEt$ | — | H |
| OH | 1 | $CH_3$ | — | $CH_2COOEt$ | — | H |
| $NO_2$ | 1 | $CH_3$ | — | $CH_2COOEt$ | — | H |
| H | 1 | COOH | — | $CH_2COOEt$ | — | H |
| Cl | 1 | COOH | — | $CH_2COOEt$ | — | H |
| F | 1 | COOH | — | $CH_2COOEt$ | — | H |
| $CF_3$ | 1 | COOH | — | $CH_2COOEt$ | — | H |
| OH | 1 | COOH | — | $CH_2COOEt$ | — | H |
| $NO_2$ | 1 | COOH | — | $CH_2COOEt$ | — | H |
| H | 1 | $CF_3$ | — | $CH_2COOEt$ | — | H |
| OH | 1 | $CF_3$ | — | $CH_2COOEt$ | — | H |
| H | 1 | $CH_2COOH$ | — | $CH_2COOEt$ | — | H |
| OH | 1 | $CH_2COOH$ | — | $CH_2COOEt$ | — | H |
| H | 1 | $CH_2CH_2COOH$ | — | $CH_2COOEt$ | — | H |
| OH | 1 | $CH_2CH_2COOH$ | — | $CH_2COOEt$ | — | H |

The invention is further defined by reference to the following preparations and examples, which are intended to be illustrative and not limiting.

All temperatures are in degrees Celsius.

PREPARATION 1

1,3-Dihydro-5-(2-fluorophenyl)-3(R)-(3'-indolyl)methyl-2H-1,4-benzodiazepin-2-one 2-Amino-2'-fluorobenzophenone (12.5 g, 58 mmole) was stirred in 100 ml of dry tetrahydrofuran in an ice bath. D-Tryptophan acid chloride hydrochloride (16 g, 62 mmole), slurried in 50 ml of tetrahydrofuran, was added over 10 minutes, and the mixture stirred 2 hours in the ice bath. The resulting solid was filtered, then added to 200 ml of methanol containing 200 ml of water. The pH was adjusted to 8.5-9.0 with 10% sodium hydroxide, the mixture was stirred for three days, then filtered. The solid was dried in vacuo at 40°.

PREPARATION 2

1,3-Dihydro-5-(2-fluorophenyl)-3-(R)-(3'-indolyl)methyl-2H-1,4-benzodiazepin-2-thione 1,3-Dihydro-5-(2-fluorophenyl)-3-(R)-(3'-indolyl)-methyl-2H-1,4-benzodiazepin-2-one (2.5 g, 6.5 mmole) and 2,4-bis-(4-methoxyphenyl)-2,4-dithioxo-1,3,2,4-dithiaphosphetane (1.6 g, 3.95 mmole) (Lawesson's reagent) were combined in toluene (35 ml) and heated at reflux under nitrogen for 45 minutes. The mixture was cooled and added directly to the top of a nine inch (23 cm) column (55 mm diameter) of silica gel (230-400 mesh) and eluted with methylene chloride ($CH_2Cl_2$), followed by a gradient of 1% to 5% (v/v) ether in $CH_2Cl_2$. The product fractions were combined and evaporated in vacuo to give the title compound as a white solid.

m.p.: 147°-148° C.

Pmr: confirmed structure of the title compound.

PREPARATION 3

1,3-Dihydro-5-(2-fluorophenyl)-3-(R)-(3'-indolyl)methyl-2H-1,4-benzodiazepin-2-hydrazone The compound from Preparation 2 (0.49 g, 1.22 mmole) and 95% hydrazine (0.24 g, 7.5 mmole) were combined in methanol (8 ml) and stirred at ambient temperature for 30 minutes. An additional 0.24 g of hydrazine was added, and the mixture was stirred another 60 minutes, then poured into ice water (100 ml). The mixture was extracted with methylene chloride ($CH_2Cl_2$) (3×50 ml) and the $CH_2Cl_2$ layers washed with water, dried over potassium carbonate, filtered, and evaporated to dryness in vacuo to give the title compound.

EXAMPLE 1

6-(2-Fluorophenyl)-4-(R)-4-(3'-indolyl)methyl-1-methyl-4H-s-triazolo[4,3-a]-1,4-benzodiazepine 1,3-Dihydro-5-(2-fluorophenyl)-3-(R)-(3'-indolyl)-methyl-2H-1,4-benzodiazepin-2-hydrazone (0.5 g, 1.26 mmole) and triethyl orthoacetate (1.15 g, 7.1 mmole) were combined in absolute ethanol (15 ml). Concentrated sulfuric acid (0.16 ml) was added and the mixture stirred at ambient temperature for 30 minutes. The acid was neutralized with saturated sodium bicarbonate solution and the mixture evaporated in vacuo. The residue was treated with water (30 ml) and extracted with methylene chloride ($CH_2Cl_2$) (3×30 ml). The $CH_2Cl_2$ layers were combined, washed with water, dried over potassium carbonate, filtered, and evaporated to dryness in vacuo. The residue was chromatographed on silica gel (230-400 mesh, nine inch (23 cm) column, 25 mm diameter, 1.5% and 4% (v/v) methanol in $CH_2Cl_2$ elution), and the product fractions evaporated to dryness in vacuo. The residue was recrystallized from ether to give the title compound: (m.p.: ca. 80° (foam)).

Analysis Calc'd for $C_{26}H_{20}FN_5.0.4Et_2O.0.5H_2O$: C, 72.04; H, 5.48; N, 15.22; Found: C, 72.05; H, 5.13; N, 15.22.

The compound showed a single spot by tlc ($R_f=0.32$, silica gel plate eluted with 5% (v/v) methanol in $CH_2Cl_2$.

The nmr spectrum was consistent with the title structure and verified the presence of ether (ca. 0.5 mole), and water.

The compound was 98.8% pure by hplc.

EXAMPLE 2

6-(2-Fluorophenyl)-4(R)-4-(3'-indolyl)methyl-1-phenyl-4H-s-triazolo[4,3-a]-1,4-benzodiazepine Following the procedure of Example 1, 230 mg (0.58 mmole) of 1,3-dihydro-5-(2-fluorophenyl)-3-(R)-(3'-indolyl)methyl-2H-1,4-benzodiazepin-hydrazone and 346 mg (1.9 mmole) of trimethyl orthobenzoate in 10 ml of ethanol were reacted to give the title compound.

The analytical sample was obtained via silica gel chromatography (chloroform-methanol 97:3 v/v elution) and was fully characterized.

tlc, hplc: greater than 96% pure.

ms (14 eV): 483(M+), 383, 354, 284.

PMR ($CDCl_3$): 4.05 (1H, dxd, J=15.9), 4.20 (1H, dxd, J=15.5), 4.34 (1H, dxd, J=9.5), 6.94 (1H, m), 7.03 (1H, m), 7.10 (1H, m), 7.19 (1H, m), 7.25–7.45 (11H, m), 7.56 (1H, m), 7.68 (2H, m), 8.14 (1H, bs, N—H).

Elemental Analysis: $C_{31}H_{22}FN_5.0.55CHCl_3$: Calc'd: N, 12.75; C, 68.99; H, 4.14. Found: N, 12.46; C, 69.21; H, 4.31.

EXAMPLE 3

6-(2-Fluorophenyl)-4(R)-4-(3'-indolyl)methyl-4H-s-triazolo[4,3-a]-1,4-benzodiazepine Following the procedure of Example 1, 230 mg (0.58 mmole) of 1,3-dihydro-5-(2-fluorophenyl)-3-(R)-(3'-indolyl)-methyl-2H-1,4-benzodiazepin-2-hydrazone and 203 mg (1.9 mmole) of trimethyl orthoformate were reacted in 5 ml of ethanol in the presence of concentrated sulfuric acid (2 drops) to give 240 mg of the title compound.

The analytical sample was prepared by silica gel chromatography (chloroform-methanol 95:5 v/v elution) and fully characterized.

tlc, hplc: greater than 98% pure.

ms (14 ev): 407 (M+), 278.

pmr ($CDCl_3$): 4.05 (1H, m), 4.17 (1H, m), 4.35 (1H, m), 6.98 (1H, t, J=9), 7.10 (1H, t, J=7), 7.15–7.7 (11H, m), 8.12 (1H, b.s., N—H), 8.64 (1H, s, C—H triazole).

Elemental Analysis: $C_{25}H_{18}FN_5.0.5CHCl_3$: Calc'd.: N, 14.99; C, 65.56; H, 3.99 Found: N, 14.96; C, 65.81; H, 4.15.

EXAMPLE 4

6-(2-Fluorophenyl)-4(R)-4-(3'-indolyl)methyl-1-dimethylaminomethyl-4H-s-triazolo[4,3-a]-1,4-benzodiazapine 6-(2-Fluorophenyl)-4-(R)-4-(3'-indolyl)methyl-4H-s-triazolo[4,3-a]-1,4-benzodiazepine (250 mg, 0.61 mmole) and dimethyl methylene ammonium chloride (80 mg, 0.8 mmole) were combined in 3 ml of degassed dimethylformamide and heated at 80° C. for 3 hours. The reaction mixture was poured into 50 ml of water, made alkaline with sodium hydroxide, and extracted with chloroform (3×75 ml). The combined organic extracts were washed with water (50 ml) and brine, then dried ($MgSO_4$) and rotoevaporated to yield 300 mg of crude product. The analytical product was obtained via silica gel chromatography (methylene chloride-methanol 95:5 v/v) and was fully characterized.

1. Prepared according to procedure in S. Kinast & L. Tietze, *Angew. Chem. Int. Ed.*, (1976) 15, 239; H. Böhme and K. Hartke, *Chem. Ber.*, (1960) 93, 1305.

tlc, hplc: greater than 96% pure.

ms (70 ev): 464 (M+), 421, 292.

pmr (CDCl$_3$): 2.63 (6H, s, N(CH$_3$)$_2$), 3.65 (2H, dxd), 4.05 (1H, dxd), 4.13 (1H, dxd), 4.28 (1H, dxd), 6.96 (1H, t), 7.07 (1H, t), 7.15–7.6 (9H, m), 7.68 (1H, d), 8.23 (1H, d), 8.27 (1H, b.s.).

Elemental Analysis: C$_{28}$H$_{25}$FN$_6$.0.22CHCL$_3$: Calc'd: N, 17.12; C, 69.05; H, 5.18. Found: N, 17.18; C, 69.00; H, 5.34.

EXAMPLE 5

2,4-Dihydro-3(R)-(3'-indolyl)methyl-6-(2-fluorophenyl)-1H-S-triazolo-[4,3-a]-1,4-benzodiazepin-1-one solvate 1,3-Dihydro-3(R)-(3'-indolyl)methyl-6-(2-fluorophenyl)-2H-1,4-benzodiazepin-2-hydrazone (160 mg, 0.40 mmole) and carbonyl diimidazole (324 mg, 2 mmole) were combined in 30 ml of dry tetrahydrofuran at room temperature. The reaction mixture was protected from moisture and allowed to stand overnight. After 14 hours at room temperature the reaction was heated to reflux for 3 hours, cooled and diluted with 150 ml of ethyl acetate. This solution was washed with water (2×50 ml) and brine. The dried organic extracts (MgSO$_4$) were concentrated to yield 300 mg of crude product. Preparative thick layer chromatography (chloroform-methanol-ammonia elution, 95:5:0.5 v/v) afforded the analytical sample.

HPLC: greater than 99% pure.

PMR (CDCL$_3$): according to theory.

MS (70 ev.): 423 (M+), 294.

Elemental Analysis: C$_{25}$H$_{18}$FN$_5$O.0.5CHCL$_3$: Calc'd: N 14.49; C 63.34; H 3.86 Found: N 14.55; C 63.65; H 4.00

EXAMPLE 6

1-Trichloromethyl-4(R)-(3'-indolyl)methyl-6-(2-fluorophenyl)-4H-S-triazolo[4,3-a]-1,4-benzodiazepine solvate To a solution of 1 ml of ethanol containing 1,3-dihydro-3(R)-(3'-indolyl)methyl-5-(2-fluorophenyl)-2H-1,4-benzodiazephine-2-hydrazone (90 mg. 0.23 mmole) and trichloroacetonitrile (79 μl, 0.79 mmole) was added 1 drop of concentrated sulfuric acid at room temperature. After four hours, 1 ml of saturated sodium bicarbonate solution was added to the reaction mixture and the solvent was removed under reduced pressure. The residue was dissolved in methylene chloride (20 ml) and washed with water (3×30 ml) and brine. The dried (MgSO$_4$) organic phase was concentrated to give 100 mg of crude product which was chromatographed on silica gel (hexaneethylacetate), 3:2 v/v) to afford the analytical sample (90 mg).

HPLC: greater than 99% pure.

PMR (CDCl$_3$): according to theory.

MS (70 ev.): 525 (M+) 523, 406, 393.

Elemental Analysis: C$_{26}$H$_{17}$Cl$_3$FN$_5$.0.5CHCL$_3$: Calc'd: N 11.98; C 54.45; H 3.01 Found: N 10.76; C 54.39; H 3.03

PREPARATION 4

1,3-Dihydro-5-(2-fluorophenyl)-3-benzyloxycarbonylamino-2H-1,4-benzodiazepin-2-thione 1,3-Dihydro-5-(2-fluorophenyl)-3-benzyloxycarbonylamino-2H-1,4-benzodiazepin-2-one (6.5 g, 16.1 mmole) and 2,4-bis-(4-methoxyphenyl)-2,4-dithioxo-1,3,2,4-dithiaphosphetane (4.9 g, 12.1 mmol) were combined in 500 ml of toluene and heated at reflux for 1.5 hours. The reaction mixture was cooled, diluted to 700 ml with ethyl acetate and washed with 10% sodium hydroxide solution (4×50 ml) and brine. The organic phase was dried (Na$_2$SO$_4$) and concentrated under reduced pressure to yield 12 g of crude product. Trituration with ethyl acetate gave 4.0 g of the analytical product as a yellow powder. Chromatography of the mother liquors on silica gel (hexane-ethyl acetate elution 1:1 v/v) afforded an additional 2.2 g of pure product: m.p. 190°–191° C.

Pmr (CDCl$_3$): confirmed structure of the title compound.

MS (14 ev): 419 (M+), 311, 284, 256, 243, 224.

Elemental Analysis: C$_{23}$H$_{18}$FN$_3$O$_2$S: Calc'd: N, 10.02; C, 65.86; H, 4.33. Found: N, 9.79; C, 65.59; H, 4.44.

PREPARATION 5

1,3-Dihydro-5-(2-fluorophenyl)-3-amino-2H-1,4-benzodiazepin-2-thione

To an equal volume mixture of methylene chloride and acetic acid (400 ml) was added 3.1 g (7.39 mmole) of 1,3-dihydro-5-(2-fluorophenyl)-3-benzyloxy carbonylamino-2H-1,4-benzodiazepin-2-thione. Hydrogen bromide gas was passed into the stirred solution for 6–8 hours. The solvent and excess reagent were removed under reduced pressure to give 8 g of the crude HBr salt as a powder. This material was suspended in methylene chloride, rendered basic with sodium hydroxide solution, and rotoevaporated to dryness. The residue was flash chromatographed on silica gel (CHCl$_3$—CH$_3$OH, 99:1 then CHCl$_3$—CH$_3$OH—NH$_3$, 90:10:1) and afforded 2.4 g of the pure amine.

Pmr (CDCl$_3$/DMSO-d$_6$): confirmed structure of the title compound.

PREPARATION 6

1,3-Dihydro-5-(2-fluorophenyl)-3-(4-chlorophenyl)carbonylamino-2H-1,4-benzodiazepin-2-thione A mixture of 1,3-dihydro-5-(2-fluorophenyl)-3-amino-2H-1,4-benzodiazepin-2-thione (200 mg, 0.70 mmole), 4-chlorobenzoic acid (120 mg, 0.77 mmole), and 1-ethyl-3-(3-dimethylaminopropyl)carbodiimide hydrochloride (150 mg, 0.77 mmole) were combined in 2 ml of dry N,N-dimethylformamide at room temperature. The pH of the homogeneous reaction mixture was then adjusted to 8 with triethylamine. The reaction mixture was protected from moisture and stirred at room temperature overnight (90% complete after 1 hour). The solvent was removed under reduced pressure and the residue dissolved in 100 ml of ethylacetate. The organic phase was then washed in succession with 10% citric acid solution (2×20 ml), saturated sodium bicarbonate solution (20 ml), and brine. The dried (MgSO$_4$) organic phase was rotoevaporated to dryness to yield 300 mg of crude product. Preparative thick layer chromatography on SiO$_2$ (hexane-ethyl acetate, 2:1) gave the analytical sample as a solvate: m.p. 156°–158° C.

Pmr (DMSO-d$_6$): confirmed structure of the title compound.

MS (14 ev): 423 (M+), 391, 284, 268, 236, 139.

Elemental Analysis: $C_{22}H_{15}ClFN_3OS$ 0.10 $C_4H_8O_2$: Calc'd: N, 9.71; C, 62.17; H, 3.68. Found: N, 9.39; C, 62.45; H, 4.01.

PREPARATION 7

1,3-Dihydro-5-(2-fluorophenyl)-3-(2-indole)carbonylamino-2H-1,4-benzodiazepin-2-thione A mixture of 1,3-dihydro-5-(2-fluorophenyl)-3-amino-2H-1,4-benzodiazepin-2-thione (400 mg, 1.40 mmole), indole-2-carboxylic acid (248 mg, 1.54 mmole), and 1-ethyl-3-(3-dimethylaminopropyl) carbodiimide hydrochloride (295 mg, 1.54 mmole) were combined in 10 ml of dry N,N-dimethylformamide at room temperature. The pH of the homogeneous reaction mixture was then adjusted to 8 with triethylamine. The reaction mixture was protected from moisture and stirred at room temperature overnight (50% complete after 1 hour). The solvent was removed under reduced pressure and the residue dissolved in 200 ml of ethylacetate. The organic phase was then washed in succession with 10% citric acid solution (2×25 ml), saturated sodium bicarbonate solution (25 ml), and brine. The dried (MgSO4) organic phase was rotoevaporated to dryness to yield 1.4 g of crude product. Preparative thick layer chromatography on SiO2 (hexane-ethyl acetate, 1:1) gave the analytical sample as a beige powder: m.p. 209°–211° C.

Pmr (CDCl3): confirmed structure of the title compound.

MS (14 ev): 428 (M+), 396, 394, 296, 293, 252, 249.

Elemental Analysis: $C_{24}H_{17}FN_4OS$ 0.15 $C_4H_8O_2$: Calc'd: N, 12.69; C, 66.89; H, 4.15. Found: N; 12.92; C, 66.69; H, 3.90.

PREPARATION 8

1,3-Dihydro-5-(2-fluorophenyl)-3-benzyloxycarbonylamino-2H-1,4-benzodiazepin-2-hydrazone Using reaction conditions identical to those described in Preparation 3, 1,3-dihydro-5-(2-fluorophenyl)-3-benzyloxycarbonylamino-2H-1,4-benzodiazepin-2-thione (1.64 g, 3.91 mmole) was converted to the title compound with 2.5 ml of hydrazine (95% in 35 ml of methanol.

PREPARATION 9

1,3-Dihydro-5-(2-fluorophenyl)-3-(4-chlorophenyl)carbonylamino-2H-1,4-benzodiazepin-2-hydrazone Using reaction conditions identical to those described in Preparation 3, 1,3-dihydro-5-(2-fluorophenyl)-3-(4-chlorophenyl)carbonylamino-2H, 1,4-benzodiazepin-2-thione (230 mg, 0.54 mmole) was converted to the title compound with 1 ml of hydrazine (95%) in 5 ml of methanol.

Preparation 10

1,3-Dihydro-5-(2-fluorophenyl)-3-(2-indole)carbonylamino-2H-1,4-benzodiazepin-2-hydrazone Using reaction conditions identical to those described in Preparation 3, 1,3-dihydro-5-(2-fluorophenyl)-3-(2-indole)-carbonylamino-2H-1,4-benzodiazepin-2-thione (1.0 g, 2.33 mmole) was converted to the title compound with 2 ml of hydrazine (95%) in 20 ml of methanol.

EXAMPLE 7

6-(2-Fluorophenyl)-4-(4-chlorophenyl)carbonylamino-4H-s-triazolo[4,3-a]-1,4-benzodiazepine Following the procedure of Example 1, 230 mg (0.54 mmole) of 1,3-dihydro-5-(2-fluorophenyl-3-(4-chlorophenyl)carbonylamino-2H-1,4-benzodiazepin-2-hydrazone and 230 mg (2.17 mmole) of trimethyl orthoformate in 5 ml of ethanol were reacted to give the title compound. The analytical sample was obtained by silica gel chromatography (chloroform-methanol, 97:3) and recrystallization from ethyl acetate ether as white needles: m.p. 250°–251° C.

Pmr (DMSO-d6): 6.38 (1H, d, J=8 Hz, C4proton), 9.36 (1H, s, triazolo proton); spectrum confirms structure.

MS (14 ev): 431 (M+), 292.

Elemental Analysis: $C_{23}H_{15}ClFN_5O$: Calc'd: N, 16.22; C, 63.97; H, 3.50. Found: N, 15.92; C, 64.14; H, 3.70.

EXAMPLE 8

6-(2-Fluorophenyl)-4-(indol-2-yl)carbonylamino-4H-s-triazolo[4,3-a]-1,4-benzodiazepine Following the procedure of Example 1, 200 mg (0.46 mmole) of 1,3-dihydro-5-(2-fluorophenyl)-3-(indol-2-yl)carbonylamino-2H-1,4-benzodiazepin-2-hydrazone and 260 mg (2.45 mmole) of trimethyl orthoformate in 5 ml of methanol were reacted to give the title compound. Preparative thick layer chromatogrpahy (chloroform-ethanol-ammonia 90:10:1) followed by recrystallization from ethyl acetate afforded the analytical sample: m.p. 291° C.

Pmr (DMSO-d6): 6.44 (1H, d, J=8 Hz, C4proton), 9.37 (1H, s, triazolo proton), 10.15 (1H, d, J=8 Hz, amide NH); spectrum confirms structure assignment.

MS (14 ev): 436 (M+), 292, 160.

Elemental Analysis: $C_{25}H_{17}FN_6O$ 0.10 $C_4H_8O_2$: Calc'd: N, 18.87; C, 68.51; H, 4.03. Found: N, 18.86; C, 68.45; H, 3.87.

EXAMPLE 9

6-(2-Fluorophenyl)-4-(indol-2-yl)carbonylamino-1-methyl-4H-s-triazolo[4,3-a]-1,4-benzodiazepine Following the procedure of Example 1, 100 mg (0.23 mmole) of 1,3-dihydro-5-(2-fluorophenyl)-3-(indol-2-yl)carbonylamino-2H-1,4-benzodiazepin-2-hydrazone and 260 mg (1.6 mmole) of triethyl orthoacetate in 5 ml of ethanol were reacted to give the title compound. Preparative thick layer chromatography (chloroform-ethanol-ammonia, 90:10:1 and then rechromatography with chloroform-methanol-ammonia 95:5:0.5) afforded the analytical sample: m.p. 294° C. (d).

Pmr (DMSO-d6): 2.6 (3 H, s, CH3), 6.32 (1H, d, J=8 Hz, C4proton), 10.10 (1H, d, J=8 Hz, amide NH), 11.10 (1H, br.s., indole NH); spectrum confirms structure and solvate.

MS (14 ev): 450 (M+), 306.

Elemental Analysis: $C_{26}H_{19}FN_6O$ 0.20 $C_4H_8O_2$: Calc'd: N, 17.96; C, 68.76; H, 4.44. Found: N, 17.86; C, 68.78; H, 4.52.

EXAMPLE 10

6-(2-Fluorophenyl)-4-benzyloxycarbonylamino-4H-s-triazolo[4,3-a]-1,4-benzodiazepine Following the procedure of Example 1, 1.39 g (3.33 mmole) of 1,3-dihydro-(5-(2-fluorophenyl)-3-benzyloxycarbonylamino-2H-1,4-benzodiazepin-2-hydrazone and 5 ml (45.7 mmole) of trimethylorthoformate in 30 ml of methanol were reacted to give the title compound. Silica gel chromatography (chloroform-methanol-ammonia 95:5:0.5 elution) followed by recrystallization from ethyl acetate-ether gave the analytical material as white rosettes: m.p. 123° C.

Pmr (CDCl$_3$): 5.03 (2H, s, benzyl protons), 6.09 (1H, d, J=9 Hz, C$_4$proton), 8.67 (1H, s, triazolo proton); spectrum confirms structure assignment.

MS (14 ev): 427 (M+), 319, 292, 287, 264, 108.

Elemental Analysis: C$_{24}$H$_{18}$FN$_5$O$_2$: Calc'd: N, 16.38; C, 67.43; H, 4.24. Found: N, 16.38; C, 67.26; H, 4.32.

Claims to the invention follow.

What is claimed is:

1. A compound of the formula:

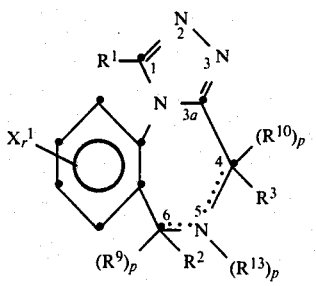

wherein

R$^1$ is H, OH, loweralkyl, cycloloweralkyl, loweralkynyl, loweralkenyl, substituted or unsubstituted phenyl (wherein the substituents are 1 or 2 of halo, loweralkyl, loweralkoxy, or hydroxy), —(CH$_2$)$_m$NR$^4$R$^5$, CX$_3^{10}$, or —(CH$_2$)$_n$COOR$^6$;

R$^2$ is H, loweralkyl, substituted or unsubstituted phenyl (wherein the substitutents are 1 or 2 of halo, loweralkyl, loweralkoxy, loweralkylthio, carboxyl, carboxyloweralkyl, nitro, —CF$_3$,

or hydroxy), or —(CH$_2$)$_m$COOR$^6$;

R$^3$ is —(CH$_2$)$_n$R$^7$,

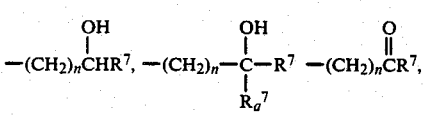

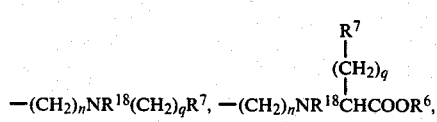

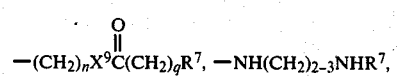

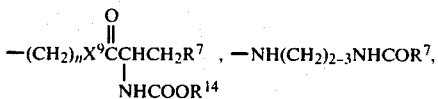

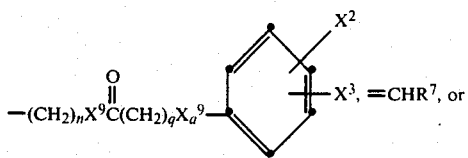

—(CH$_2$)$_n$NR$^{18}$SO$_2$(CH$_2$)$_q$R$^7$,

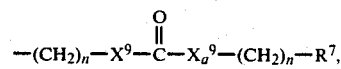

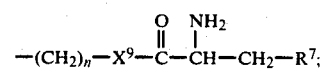

R$^4$ and R$^5$ are independently H, loweralkyl, or cycloloweralkyl or are connected to form a hetero ring

wherein n is 2–6;

R$^6$ is H, loweralkyl, cycloloweralkyl, substituted or unsubstituted phenyl (wherein the substituents are 1 or 2 of halo, loweralkyl, loweralkoxy, nitro, or CF$_3$), or substituted or unsubstituted phenylloweralkyl (wherein the substituents are 1 or 2 of halo, loweralkyl, loweralkoxy, nitro, or CF$_3$);

R$^7$ and R$_a^7$ are independently α- or β-naphthyl, substituted or unsubstituted phenyl (wherein the substituents are 1 to 2 of halo, —NO$_2$, —OH, —NR$^4$R$^5$, cyano, phenyl, trifluoromethyl, acetylamino, acetyloxy, loweralkylthio, SCF$_3$, —C≡CH, CH$_2$SCF$_3$, OCHF$_2$, SH, S-phenyl, PO$_3$H, or loweralkoxy),

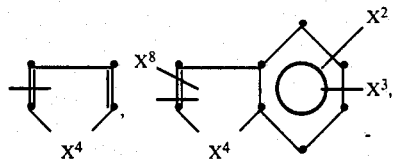

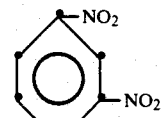

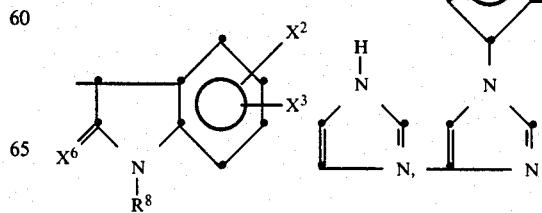

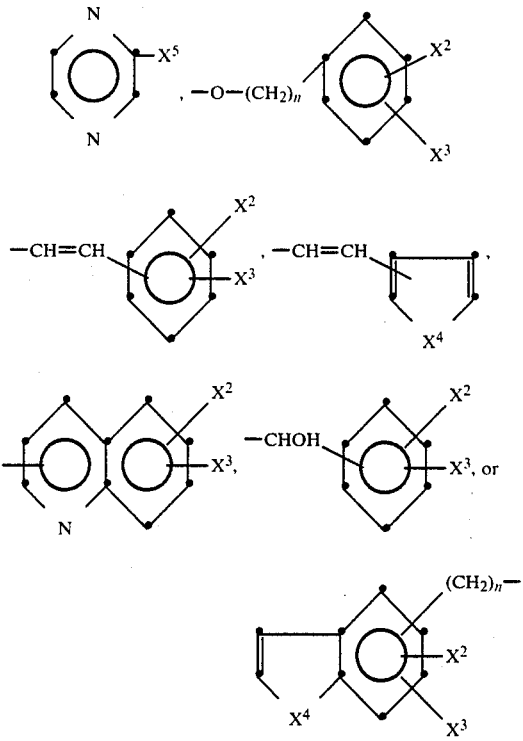

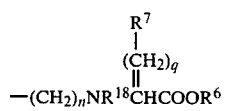

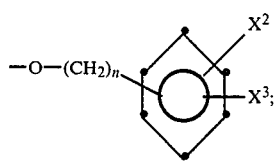

(with the proviso that q is not 0 or 1 in —(CH$_2$)$_n$NH(CH$_2$)$_q$R$^7$ and that q is not 0 in $$-(CH_2)_nNR^{18}\overset{\overset{\overset{R^7}{|}}{(CH_2)_q}}{C}HCOOR^6$$

when R$^7$ or R$_a^7$ is

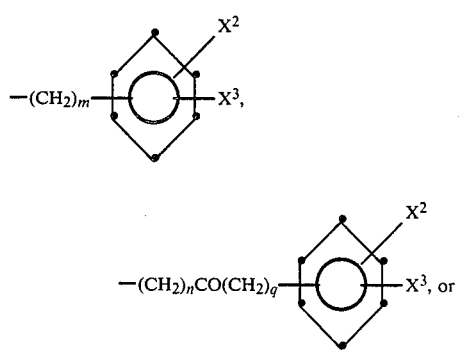

R$^8$ is H, loweralkyl, cycloloweralkyl, —(CH$_2$)$_m$CONH$_2$, —(CH$_2$)$_m$COOR$^6$, —(CH$_2$)$_n$-cycloloweralkyl, —(CH$_2$)$_m$NR$_4$R$_5$,

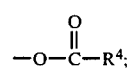

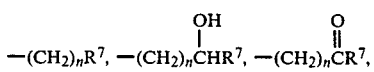

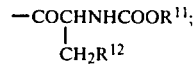

R$^9$ and R$^{10}$ are independently H, —OH, or —CH$_3$;
R$^{11}$ and R$^{12}$ are independently loweralkyl or cycloloweralkyl;
R$^{13}$ is H, loweralkyl, acyl, O, or cycloloweralkyl;
R$^{14}$ is loweralkyl or phenylloweralkyl;
R$^{18}$ is H, loweralkyl, or acyl;
m is 1–4;
n is 0–4;
p is 0 when its adjacent === is unsaturated or when R$^3$ is =CHR$^7$, and it is 1 when its adjacent === is saturated, except that when R$^{13}$ is O, p=1 and === is unsaturated;
q is 0–4;
r is 1 or 2;
X$^1$ is H, —NO$_2$, CF$_3$ CN, OH, loweralkyl, halo, loweralkylthio, loweralkoxy, —(CH$_2$)$_n$COOR$^6$, —NR$^4$R$^5$, or $$O-\overset{\overset{O}{||}}{C}-R^4;$$

X$^2$ and X$^3$ are independently H, —OH, —NO$_2$, halo, loweralkylthio, loweralkyl, loweralkoxy or $$-O-\overset{\overset{O}{||}}{C}-R^4;$$

X$^4$ is S, O, CH$_2$, or NR$^8$;
X$^5$ is H, CF$_3$, CN, —COOR$^6$, NO$_2$, or halo;
X$^6$ is O or HH;
X$^8$ is H or loweralkyl;
X$^9$ and X$_a^9$ are independently NR$^{18}$, O
X$^{10}$ is F, Cl, Br;
=== is a saturated or unsaturated bond, such that both bonds in the seven-membered ring of Formula I may be saturated (single bonds), but both may not be unsaturated (double bonds),
and the pharmaceutically acceptable salts thereof.

2. A compound of claim 1 wherein:
R$^1$ is H, loweralkyl, unsubstituted phenyl —(CH$_2$)$_n$COOR$^6$, or —(CH$_2$)$_m$NR$^4$R$^5$;
R$^2$ is substituted or unsubstituted phenyl (wherein the substituents are 1 or 2 of halo, loweralkyl, loweralkoxy, carboxyl, carboxyloweralkyl, nitro, —CF$_3$, or hydroxy), or —(CH$_2$)$_m$COOR$^6$;
R$^3$ is $$-(CH_2)_nR^7,\ -(CH_2)_n\overset{\overset{OH}{|}}{C}HR^7,\ -(CH_2)_n\overset{\overset{O}{||}}{C}R^7,$$

$$-(CH_2)_nNH(CH_2)_qR^7,\ -(CH_2)_nN\overset{\overset{\overset{R^7}{|}}{(CH_2)_q}}{|}HCHCOOR^6,$$

$$-(CH_2)_n NH\overset{\overset{O}{||}}{C}(CH_2)_qR^7,\ -NH(CH_2)_{2-3}NHR^7,$$

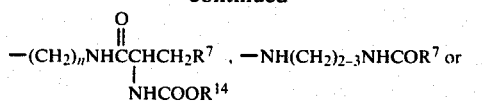, 

$R^4$ and $R^5$ are independently H or loweralkyl;
$R^6$ is H or loweralkyl;
$R^7$ is α- or β-naphthyl.

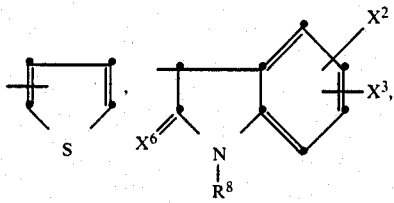

substituted or unsubstituted phenyl (wherein the substituents are 1 to 2 of halo, —NO$_2$, —OH, —NR$^4$R$^5$, loweralkyl, CF$_3$, loweralkoxy loweralkylthio, CN, —C≡CH, SCF$_3$,

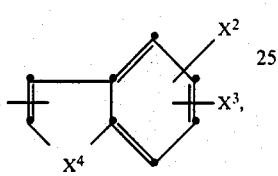

OCHF$_2$, or SPh),

$R^8$ is H, loweralkyl, or

—COCHNHCOOR$^{11}$;
    |
   CH$_2$R$^{12}$ $R^9$ and $R^{10}$ are independently H, —OH, or —CH$_3$;
$R^{11}$ and $R^{12}$ are independently loweralkyl;
$R^{13}$ is H, O, loweralkyl, or acyl;
$R^{14}$ is loweralkyl;
m is 1–4;
n is 0–4;
p is 0 when its adjacent ═══ is unsaturated and 1 when its adjacent ═══ is saturated, except that when $R^{13}$ is O, p=1 and ═══ is unsaturated.
q is 0–4;
r is 1 or 2;

$X^1$ is H, —NO$_2$, CF$_3$, CN, OH, loweralkyl, halo, loweralkylthio, loweralkoxy, —(CH$_2$)$_n$COOR$^6$, or —NR$^4$R$^5$;
$X^2$ and $X^3$ are independently H, —OH, —NO$_2$, halo, loweralkylthio, loweralkyl, or loweralkoxy;
$X^4$ is S, O, or NR$^8$;
$X^6$ is O or NH;
═══ is a saturated or unsaturated bond
and the pharmaceutically acceptable salts thereof.

3. A compound of claim 2 wherein:
$R^1$ is H, methyl, ethyl, unsubstituted phenyl, carboxyl, carboxymethyl, or —CH$_2$N(CH$_3$)$_2$;
$R^2$ is substituted or unsubstituted phenyl (wherein the substitutents are 1 or 2 of halo or carboxyl), or —(CH$_2$)$_{1-2}$COOR$^6$;
$R^3$ is

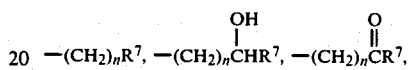

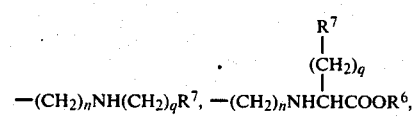

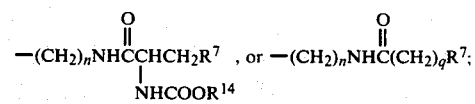

$R^6$ is H or loweralkyl;
$R^7$ is α- or β-naphthyl,

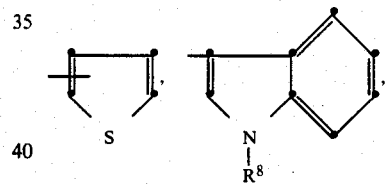

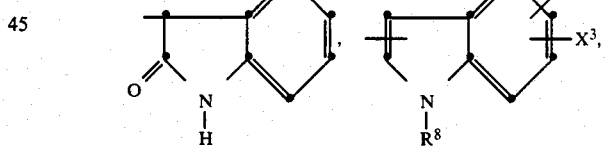

substituted phenyl (wherein the substituents are 1 or 2 of halo, loweralkyl, or CF$_3$), or

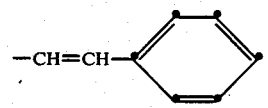

$R^8$ is H, methyl, or ethyl;
$R^9$ and $R^{10}$ are independently H, —OH, or —CH$_3$;
$R^{13}$ is H, methyl or formyl;
$R^{14}$ is t-butyl;
n is 0–4;
p is 0 when its adjacent ═══ is unsaturated and 1 when its adjacent ═══ is saturated;
q is 0–4;
r is 1 or 2;

$X^1$ is H, —NO$_2$, CF$_3$, CN, OH, or halo;
$X^2$ and $X^3$ are independently H, —OH, —NO$_2$, or halo;
≡ is a saturated or unsaturated bond
and the pharmaceutically acceptable salts thereof.

4. A compound of claim 3 wherein:
$R^1$ is H, methyl, or carboxyl;
$R^2$ is phenyl, o-fluorophenyl, p-fluorophenyl, o-chlorophenyl, p-chlorophenyl, o-carboxyphenyl, 2,6-difluorophenyl, —CH$_2$COOEt, —CH$_2$COO—t—Bu, —CH$_2$CH$_2$COOEt, or —CH$_2$CH$_2$COOt—Bu;
$R^3$ is —(CH$_2$)$_{1-2}$R$^7$, —CHR$^7$, —CR$^7$, —(CH$_2$)$_{0-1}$NH(CH$_2$)$_{1-2}$R$^7$,
            OH    O —(CH$_2$)$_{0-1}$NHCHCOOR$^6$, —(CH$_2$)$_{0-1}$NHC(CH$_2$)$_{0-2}$—R$^7$, or
              R$^7$           O

—(CH$_2$)$_{0-1}$NHCOCHCH$_2$R$^7$ ,
                  NHCOOR$^{14}$ and the stereochemistry relates to D-tryptophan;
$R^6$ is H, methyl, or ethyl;
$R^7$ is α- or β-naphthyl,

[thiophene structure], [indole structure with $X^2$, $X^3$ and NH], [indole structure with $X^2$, $X^3$ and N-CH$_3$]

or mono- or dihalophenyl;
$R^9$ and $R^{10}$ are independently H or —OH;
$R^{13}$ is H;
$R^{14}$ is t-butyl;
p is 0 when its adjacent ≡ is unsaturated and 1 when its adjacent ≡ is saturated;
r is 1;
$X^1$ is H, chloro, fluoro, or nitro;
$X^2$ and $X^3$ are independently H, —OH, fluoro, or chloro;
≡ is a saturated or unsaturated bond
and the pharmaceutically acceptable salts thereof.

5. A compound of claim 1 which is
6-(2-Fluorophenyl)-4-(R)-4-(3'-indolyl)methyl-1-methyl-4 H-s-triazolo[4,3-a]-1,4-benzodiazepine;
6-(2-Fluorophenyl)-4(R)-4-(3'-indolyl)methyl-1-phenyl-4H-triazolo[4,3-a]-1,4-benzodiazpine;
6-(2-Fluorophenyl)-4(R)-4-(3'-indolyl)methyl-4H-s-triazolo [4,3-a]-1,4-benzodiazepine;
6-(2-Fluorophenyl)-4(R)-4-(3'-indolyl)methyl-1-dimethylaminomethyl-4H-s-triazolo[4,3-a]-1,4-benzodiazepine;
2,4-Dihydro-3(R)-(3'-indolyl)methyl-6-(2-fluorophenyl)-1H-S-triazolo [4,3-a]-1,4-benzodiazepin-1-one;
1-Trichloromethyl-4(R)-(3'-indolyl)methyl-6-(2-fluorophenyl)-4H-S-triazolo[4,3-a]-1,4-benzodiazepine;
6-(2-Fluorophenyl)-4-(4-chlorophenyl)carbonylamino-4H-s-triazolo[4,3-a]-1,4-benzodiazepine;
6-(2-Fluorophenyl)-4-(indol-2-yl)carbonylamino-4H-s-triazolo[4,3-a]-1,4-benzodiazepine;
6-(2-Fluorophenyl)-4-(indol-2-yl)carbonylamino-1-methyl-4H-s-triazolo[4,3-a]-1,4-benzodiazepine; or
6-(2-Fluorophenyl)-4-benzyloxycarbonylamino-4H-s-triazolo[4,3-a]-1,4-benzodiazepine.

6. A compound of claim 1 having the formula:

[structure of triazolobenzodiazepine with $R^1$, $R^3$, and F substituents]

wherein
$R^1$ is H or CH$_3$; and
$R^3$ is —NH—CO—indol—2—yl, —NH—CO—3—chlorophenyl, or —NH—CO—O—CH$_2$—phenyl.

7. A compound of claim 6 wherein:
$R^3$ is

[structure: NH—CO—indole]

8. A pharmaceutical composition useful for treating gastrointestinal disorders, central nervous system disorders, or regulating appetite in mammals, comprising a pharmaceutically effective amount of a compound of Formula I of claim 1 and an acceptable pharmaceutical carrier.

9. A pharmaceutical composition of claim 8 useful for treating gastrointestinal disorders, central nervous system disorders, or regulating appetite in mammals, comprising a pharmaceutically effective amount of a compound of Formula I wherein:
$R^1$ is H, loweralkyl, unsubstituted phenyl —(CH$_2$)$_n$COOR$^6$, or —(CH$_2$)$_m$NR$^4$R$^5$;
$R^2$ is substituted or unsubstituted phenyl (wherein the substituents are 1 or 2 of halo, loweralkyl, loweralkoxy, carboxyl, carboxyloweralkyl, nitro, —CF$_3$, or hydroxy), or —(CH$_2$)$_m$COOR$^6$;
$R^3$ is —(CH$_2$)$_n$R$^7$, —(CH$_2$)$_n$CHR$^7$, —(CH$_2$)$_n$CR$^7$,
                    |                    ||
                    OH                   O —(CH$_2$)$_n$NH(CH$_2$)$_q$R$^7$, —(CH$_2$)$_n$NHCHCOOR$^6$,
                                              |
                                              (CH$_2$)$_q$
                                              |
                                              R$^7$ O
           ||
—(CH$_2$)$_n$NHC(CH$_2$)$_q$R$^7$, —NH(CH$_2$)$_n$NHR$^7$, O
           ||
—(CH$_2$)$_n$NHCCH$_2$R$^7$ , —NH(CH$_2$)$_n$NHCOR$^7$,
           |
           NHCOOR$^{14}$ O
                          ||
or —(CH$_2$)$_n$NHCNH(CH$_2$)$_n$R$^7$;

R$^4$ and R$^5$ are independently H or loweralkyl;
R$^6$ is H or loweralkyl;
R$^7$ is α- or β-naphthyl,

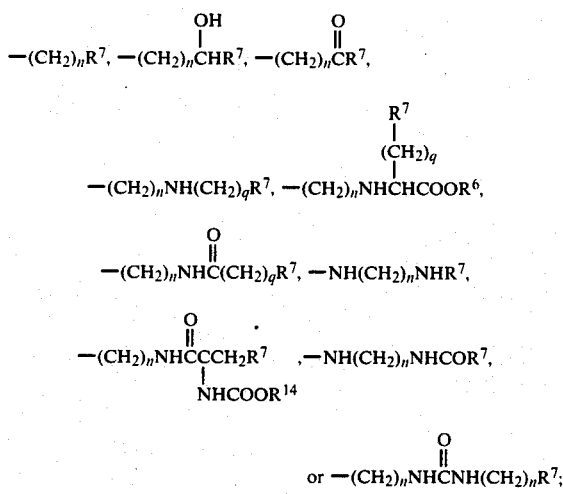

substituted or unsubstituted phenyl (wherein the substituents are 1 or 2 of halo, —NO$_2$, —OH, —NR$^4$R$^5$, loweralkyl, loweralkoxy, CF$_3$, loweralkylamino, CN, C≡CH, SCF$_3$,

O
           ||
           OCCH$_3$,

OCHF$_2$, or SPh);

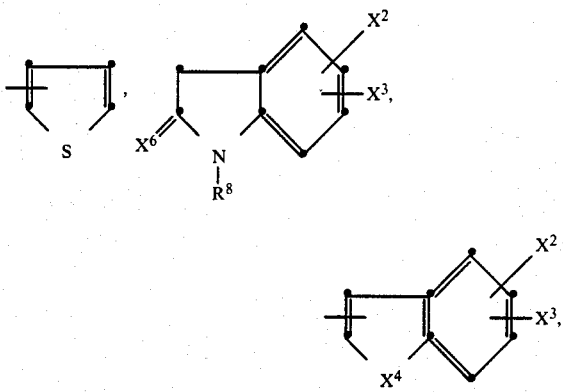

R$^8$ is H, loweralkyl, or

—COCHNHCOOR$^{11}$;
    |
    CH$_2$R$^{12}$

R$^9$ and R$^{10}$ are independently H, —OH, or —CH$_3$;
R$^{11}$ and R$^{12}$ are independently loweralkyl;

R$^{13}$ is H, O, loweralkyl, or acyl;
R$^{14}$ is loweralkyl;
m is 1-4;
n is 0-4;
p is 0 when its adjacent === is unsaturated and 1 when its adjacent === is saturated, except that when R$^{13}$ is O, p=1 and === is unsaturated;
q is 0-4;
r is 1 or 2;
X$^1$ is H, —NO$_2$, CF$_3$, CN, OH, loweralkyl, halo, loweralkylthio, loweralkoxy, —(CH$_2$)$_n$COOR$^6$, or —NR$^4$R$^5$;
X$^2$ and X$^3$ are independently H, —OH, —NO$_2$, halo, loweralkylthio, loweralkyl, or lower-alkoxy;
X$^4$ is S, O, or NR$^8$;
X$^6$ is O or HH;
=== is a saturated or unsaturated bond
and the pharmaceutically acceptable salts thereof.

10. A pharmaceutical composition according to claim 8, wherein the mammals are humans.

11. A method of treating gastrointestinal disorders, central nervous system disorders, or regulating appetite in mammals which comprises administering to said mammals a pharmaceutically effective amount of a compound of Formula I of claim 1.

12. A method of claim 11 of treating gastrointestinal disorders in humans which comprises administering a pharmaceutically effective amount of a compound of Formula I wherein:

R$^1$ is H, loweralkyl, unsubstituted phenyl —(CH$_2$)$_n$COOR$^6$, or —(CH$_2$)$_m$NR$^4$R$^5$;
R$^2$ is substituted or unsubstituted phenyl (wherein the substituents are 1 or 2 of halo, loweralkyl, loweralkoxy, carboxyl, carboxyloweralkoxy, nitro, —CF$_3$, or hydroxy), or —(CH$_2$)$_m$COOR$^6$;
R$^3$ is —(CH$_2$)$_n$R$^7$, —(CH$_2$)$_n$CHR$^7$, —(CH$_2$)$_n$CR$^7$,
                    |                    ||
                    OH                   O —(CH$_2$)$_n$NH(CH$_2$)$_q$R$^7$, —(CH$_2$)$_n$NHCHCOOR$^6$,
                                              |
                                              (CH$_2$)$_q$
                                              |
                                              R$^7$ O
           ||
—(CH$_2$)$_n$NHC(CH$_2$)$_q$R$^7$, —NH(CH$_2$)$_{2-3}$NHR$^7$, O
           ||
—(CH$_2$)$_n$NHCCH$_2$R$^7$ , or —NH(CH$_2$)$_{2-3}$NHCOR$^7$,
           |
           NHCOOR$^{14}$ O
                          ||
or —(CH$_2$)$_n$NHCNH(CH$_2$)$_n$R$^7$;

R$^4$ and R$^5$ are independently H or loweralkyl;
R$^6$ is H or loweralkyl;
R$^7$ is α- or β-naphthyl,

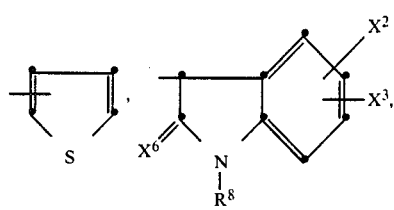

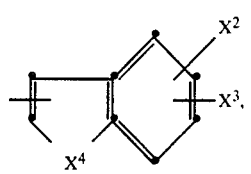

substituted or unsubstituted phenyl (wherein the substituents are 1 to 2 of halo, —NO$_2$, —OH, —NR$^4$R$^5$, loweralkyl, loweralkoxy, CF$_3$, loweralkylthio, CN, C≡CH, SCF$_3$,

OCHF$_2$, or SPh);

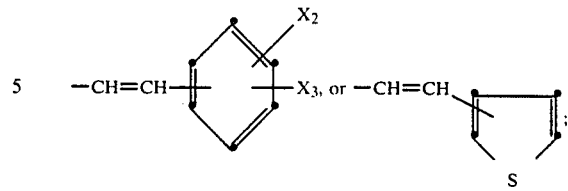

R$^8$ is H, loweralkyl, or

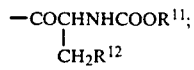

R$^9$ and R$^{10}$ are independently H, —OH, or —CH$_3$;
R$^{11}$ and R$^{12}$ are independently loweralkyl;
R$^{13}$ is H, O, loweralkyl, or acyl;
R$^{14}$ is loweralkyl;
m is 1–4;
n is 0–4;
p is 0 when its adjacent === is unsaturated and 1 when its adjacent === is saturated, except that when R$^{13}$ is O, p=1 and === is unsaturated;
q is 0–4;
r is 1 or 2;
X$^1$ is H, —NO$_2$, CF$_3$, CN, OH, loweralkyl, halo, loweralkylthio, loweralkoxy, —(CH$_2$)$_n$COOR$^6$, or —NR$^4$R$^5$;
X$^2$ and X$^3$ are independently H, —OH, —NO$_2$, halo, loweralkylthio, loweralkyl, or loweralkoxy;
X$^4$ is S, O, or NR$^8$;
X$^6$ is O or HH;
=== is a saturated or unsaturated bond
and the pharmaceutically acceptable salts thereof.

* * * * *